(12) United States Patent
Keller et al.

(10) Patent No.: US 7,365,672 B2
(45) Date of Patent: Apr. 29, 2008

(54) DETECTION OF A CONCEALED OBJECT

(75) Inventors: Paul E. Keller, Richland, WA (US); Thomas E. Hall, Kennewick, WA (US); Douglas L. McMakin, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 165 days.

(21) Appl. No.: 10/697,965

(22) Filed: Oct. 30, 2003

(65) Prior Publication Data

US 2004/0140924 A1 Jul. 22, 2004

Related U.S. Application Data

(63) Continuation-in-part of application No. 10/607,552, filed on Jun. 26, 2003, now Pat. No. 6,876,322, and a continuation-in-part of application No. 10/301,552, filed on Nov. 21, 2002, now Pat. No. 6,703,964, which is a continuation of application No. 09/810,054, filed on Mar. 16, 2001, now Pat. No. 6,507,309.

(51) Int. Cl.
*G01S 13/04* (2006.01)
(52) U.S. Cl. .......................................... 342/22; 342/179
(58) Field of Classification Search ............... 342/22, 342/27, 42, 44, 179
See application file for complete search history.

(56) References Cited

U.S. PATENT DOCUMENTS

| 3,689,772 A | 9/1972 | George et al. |
|---|---|---|
| 3,713,156 A | 1/1973 | Pothier |
| 3,755,810 A | 8/1973 | Latham et al. |
| 3,990,436 A | 11/1976 | Ott |
| 4,635,367 A | 1/1987 | Vigede |
| 4,705,401 A | 11/1987 | Addleman et al. |
| 4,737,032 A | 4/1988 | Addleman et al. |
| 4,829,303 A | 5/1989 | Zebker et al. |
| 4,910,523 A | 3/1990 | Huguenin et al. |
| 4,916,634 A | 4/1990 | Collins et al. |
| 5,047,783 A | 9/1991 | Hugenin |

(Continued)

FOREIGN PATENT DOCUMENTS

EP 0 636 898 A1 2/1995

(Continued)

OTHER PUBLICATIONS

*Combined Illumination Cylindrical Millimeter-Wave Imaging Technique for Concealed Weapon Detection*, Sheen, McMakin and Hall, Pacific Northwest National Laboratory, (date unknown).

(Continued)

*Primary Examiner*—Isam Alsomiri
(74) *Attorney, Agent, or Firm*—Klarquist Sparkman, LLP

(57) ABSTRACT

Disclosed are systems, methods, devices, and apparatus to determine if a clothed individual is carrying a suspicious, concealed object. This determination includes establishing data corresponding to an image of the individual through interrogation with electromagnetic radiation in the 200 MHz to 1 THz range. In one form, image data corresponding to intensity of reflected radiation and differential depth of the reflecting surface is received and processed to detect the suspicious, concealed object.

31 Claims, 18 Drawing Sheets

U.S. PATENT DOCUMENTS

| | | | |
|---|---|---|---|
| 5,060,393 | A | 10/1991 | Silverman et al. |
| 5,073,782 | A | 12/1991 | Huguenin et al. |
| 5,081,456 | A | 1/1992 | Michiguchi et al. |
| 5,142,255 | A | 8/1992 | Chang et al. |
| 5,170,170 | A | 12/1992 | Soumekh |
| 5,227,797 | A | 7/1993 | Murphy |
| 5,227,800 | A | 7/1993 | Huguenin et al. |
| 5,274,714 | A | 12/1993 | Hutcheson et al. |
| 5,367,552 | A | 11/1994 | Peschmann |
| 5,414,803 | A | 5/1995 | Malzbender |
| 5,455,587 | A | 10/1995 | Schneider |
| 5,455,590 | A | 10/1995 | Collins et al. |
| 5,557,283 | A | 9/1996 | Sheen et al. |
| 5,600,303 | A | 2/1997 | Husseiny et al. |
| 5,640,589 | A | 6/1997 | Takayama et al. |
| 5,680,528 | A | 10/1997 | Korszun |
| 5,720,708 | A | 2/1998 | Lu et al. |
| 5,740,800 | A | 4/1998 | Hendrickson et al. |
| 5,747,822 | A | 5/1998 | Sinclair et al. |
| 5,796,363 | A | 8/1998 | Mast |
| 5,833,599 | A | 11/1998 | Schrier et al. |
| 5,835,054 | A | 11/1998 | Warhus et al. |
| 5,857,030 | A | 1/1999 | Gaborski et al. |
| 5,859,609 | A | 1/1999 | Sheen et al. |
| 5,864,640 | A | 1/1999 | Miramonti et al. |
| 5,870,220 | A | 2/1999 | Migdal et al. |
| 5,953,448 | A | 9/1999 | Liang |
| 5,956,525 | A | 9/1999 | Minsky |
| 5,963,667 | A | 10/1999 | Hashimoto et al. |
| 5,995,014 | A | 11/1999 | DiMaria |
| 6,014,099 | A | 1/2000 | Bennett et al. |
| 6,018,562 | A | 1/2000 | Willson |
| 6,038,337 | A | 3/2000 | Lawrence et al. |
| 6,057,761 | A | 5/2000 | Yuki |
| 6,075,455 | A | 6/2000 | DiMaria et al. |
| 6,081,750 | A | 6/2000 | Hoffberg et al. |
| 6,088,295 | A | 7/2000 | Altes |
| 6,144,388 | A | 11/2000 | Bornstein |
| 6,253,164 | B1 | 6/2001 | Rohm et al. |
| 6,271,856 | B1 | 8/2001 | Krishnamurthy |
| 6,324,532 | B1 | 11/2001 | Spence et al. |
| 6,359,582 | B1 | 3/2002 | MacAleese et al. |
| 6,373,963 | B1 | 4/2002 | Demers et al. |
| 6,377,865 | B1 | 4/2002 | Edelsbrunner et al. |
| 6,418,424 | B1 | 7/2002 | Hoffberg et al. |
| 6,441,734 | B1 | 8/2002 | Gutta et al. |
| 6,480,141 | B1 | 11/2002 | Toth et al. |
| 6,507,309 | B2 | 1/2003 | McMakin et al. |
| 6,542,249 | B1 | 4/2003 | Kofman et al. |
| 6,546,309 | B1 | 4/2003 | Gazzuolo |
| 6,639,684 | B1 | 10/2003 | Knighton et al. |
| 6,690,474 | B1 | 2/2004 | Shirley |
| 6,700,526 | B2 | 3/2004 | Witten |
| 6,703,964 | B2 | 3/2004 | McMakin et al. |
| 6,734,849 | B2 | 5/2004 | Dimsdale et al. |
| 6,777,684 | B1* | 8/2004 | Volkov et al. ............ 250/341.1 |
| 6,876,322 | B2 | 4/2005 | Keller |
| 6,927,691 | B2* | 8/2005 | Yukl ...................... 340/568.1 |
| 7,034,746 | B1 | 4/2006 | McMakin et al. |
| 7,124,044 | B2 | 10/2006 | Witten |
| 2002/0130804 | A1 | 9/2002 | McMakin et al. |
| 2002/0150304 | A1* | 10/2002 | Ockman ..................... 382/260 |
| 2002/0158368 | A1 | 10/2002 | Wirth, Jr. |
| 2002/0167726 | A1 | 11/2002 | Barman et al. |
| 2003/0034444 | A1 | 2/2003 | Chadwick et al. |
| 2003/0053698 | A1 | 3/2003 | Ferguson |
| 2003/0076254 | A1 | 4/2003 | Witten |
| 2003/0086525 | A1 | 5/2003 | Rhee et al. |
| 2003/0117310 | A1 | 6/2003 | Kikuchi et al. |
| 2003/0125622 | A1 | 7/2003 | Schweikard et al. |
| 2003/0128150 | A1 | 7/2003 | McMakin et al. |
| 2003/0137646 | A1 | 7/2003 | Hoffman et al. |
| 2003/0163042 | A1 | 8/2003 | Salmon |
| 2003/0179126 | A1 | 9/2003 | Jablonski et al. |
| 2004/0023612 | A1 | 2/2004 | Kriesel |
| 2004/0090359 | A1 | 5/2004 | McMakin et al. |
| 2004/0263379 | A1 | 12/2004 | Keller et al. |
| 2005/0234383 | A1 | 10/2005 | Dougal |
| 2006/0066469 | A1 | 3/2006 | Foote et al. |

FOREIGN PATENT DOCUMENTS

| | | |
|---|---|---|
| GB | 2034554 | 6/1980 |
| GB | 2083715 | 3/1982 |
| WO | WO 02/17231 A2 | 2/2002 |

OTHER PUBLICATIONS

Abbott, "Personal Surveillance System," *IBM Technical Disclosure Bulletin*, vol. 12, No. 7, pp. 1119-1120 (Dec. 1969).

Ahles, "The Caesar Project," downloaded from thunder.temple.edu/~mridenou/pe204/BodyAnthroCaesar.html, 2 pp. (document marked as published on Feb. 11, 1999).

Aoki et al., "Diagnosis of Under-Snow Radar Images by Three Dimensional Displaying Technique in Holographic Imaging Radar," *Proc. of IGARSS '87 Symposium*, pp. 571-576 (May 18-21, 1987).

Boyer et al., "Reconstruction of Ultrasonic Images by Backward Propagation," Ch. 18, pp. 333-349 (1970).

Bruner, "An Introduction to the Body Measurement System for Mass Customized Clothing," downloaded from http://www.techexchange.com/thelibrary/bmsdes.html, 11 pp. (document marked as published Jan. 2004).

Collins, "Error Analysis in Scanned Holography," Thesis, Oregon State University (1970).

Cookson, "Body scanners to shape our shopping," London, 1 p. (dated at least as early as Dec. 1, 2000).

Cyberware, "Body Measurement/Garment Fitting Software," downloaded from www.cyberware.com/pressRelease/digisize_PR1.html, 2 pp.(document marked as published on Aug. 9, 1999).

Cyberware, "Cyberware Extracts Tailor Measurements from 3D Scan Data," downloaded from www.cyberware.com/pressReleases/arn.html, 2 pp. (document marked as published on Aug. 1, 1997).

Cyberware, "Cyberware Whole Body Scanning," downloaded from www.cyberware.com/products/WholeBody.html, 3 pp. (document marked as last updated on Jun. 22, 1999).

Cyberware, "Laser Sizes Up Your Body, Fits Your Clothing," downloaded from www.cyberware.com/pressReleases/digisize_PR2.html, 2 pp. (document marked as published on Aug. 9, 1999).

Cyberware, "The World's First Whole Body Scanners Bring True Human Forms to Computer Graphics," downloaded from www.cyberware.com/pressReleases/firstWB.html, 1 p. (document marked as published on May 11, 1995).

Farhat, "High Resolution Microwave Holography and the Imaging of Remote Moving Objects," *Optical Engineering*, vol. 14, No. 5, pp. 499-505 (1975).

Fujita et al., "Polarimetric Calibration of the SIR-C C-Band Channel Using Active Radar Calibrators and Polarization Selective Dihedrals," *IEEE Transactions on Geoscience and Remote Sensing*, vol. 36, No. 6, pp. 1872-1878 (1998).

Hildebrand et al., "An Introduction to Acoustical Holography," pp. vii, 20-21 (1974).

Keller et al., "Privacy Algorithm for Cylindrical Holographic Weapons Surveillance System," *IEEE Aerospace and Electronic Systems Magazine*, vol. 15, No. 2, pp. 17-24 (2000).

McMakin et al., "Cylindrical Holographic Imaging System Privacy Algorithm Final Report," *Pacific Northwest National Laboratory*, Richland, WA (1999).

McMakin et al., "Detection of Concealed Weapons and Explosives on Personnel Using a Wide-band Holographic Millimeter-wave Imaging System," *American Defense Preparedness Association Security Technology Division Joint Security Technology Symposium*, Williamsburg, Va. (1996).

McMakin et al., "Wideband, millimeter-wave, holographic weapons surveillance system," *Proceedings of the SPIE—EUROPTO European Symposium on Optics for Environmental and Public Safety*, vol. 2511, pp. 131-141 (1995).

Michelson et al., "A Calibration Algorithm for Circular Polarimetric Radars," *Journal of Electromagnetic Waves and Applications*, vol. 11, pp. 659-674 (1997).

Osumi et al., "Detection of Buried Objects," *IEE Proceedings*, vol. 135, Pt. F, No. 4 (Aug. 1988).

SAE International, downloaded from www.sae.org/technicalcommittees, 6 pp. (downloaded on Feb. 3, 2000).

Sheen et al., "Concealed explosive detection on personnel using a wideband holographic millimeter-wave imaging system," *Proceedings of the SPIE—AEROSENSE Aerospace/Defense Sensing and Controls*, vol. 2755, pp. 503-513 (1996).

Sheen et al., "Cylindrical millimeter-wave imaging technique for concealed weapon detection," *Proceedings of the SPIE—26th AIPR Workshop: Exploiting New Image Sources and Sensors*, vol. 3240, pp. 242-250 (Mar. 1998).

Sheen et al., "Three-Dimensional Millimeter-Wave Imaging for Concealed Weapon Detection," *IEEE Transactions on Microwave Theory and Techniques*, vol. 49, No. 9, pp. 1581-1592 (2001).

Sinclair et al., "Passive millimetre wave imaging in security scanning," *Proc. SPIE*, vol. 4032, pp. 40-45 (2000).

Soumekh, "Fourier Array Imaging," Published by PTR Prentice Hall, Englewood Cliffs, NJ, pp. 339-348 (1994).

Tricoles et al., "Microwave Holography: Applications and Techniques," *Proceedings of the IEEE*, vol. 65, No. 1, pp. 108-121 (Jan. 1977).

Yngvesson et al., "Endfire Tapered Slot Antennas on Dielectric Substrates," *IEEE Trans. on Antennas and Propagation*, vol. AP-33, No. 12, pp. 1392-1400 (Dec. 1985).

Yueh et al., "Calibration of polarimetric radars using in-scene reflectors," *Journal of Electromagnetic Waves and Applications*, vol. 4, No. 1, pp. 27-48 (1990).

Keller et al., "Privacy Algorithm for Airport Passenger Screening Portal," *Proc. SPIE*, vol. 4055, pp. 476-483 (Apr. 2000).

Keller et al., "Pulse-Coupled Neural Networks for Medical Image Analysis," *Proc. SPIE*, vol. 3722, pp. 444-451 (Apr. 1999).

McMakin et al., "Millimeter wave, high-resolution, holographic surveillance system," *Proc. SPIE*, vol. 2092, pp. 525-535 (1993).

* cited by examiner

DETECTION OF A CONCEALED OBJECT

CROSS-REFERENCE TO RELATED APPLICATIONS

The present application is a continuation-in-part of U.S. patent application Ser. No. 10/607,552 filed 26 Jun. 2003 now U.S. Pat. No. 6,876,322 and is a continuation-in-part of U.S. patent application Ser. No. 10/301,552 filed 21 Nov. 2002 now U.S. Pat. No. 6,703,964, which is a continuation of U.S. patent application Ser. No. 09/810,054 filed 16 Mar. 2001 (now U.S. Pat. No. 6,507,309). The above-indicated patent and patent applications are each hereby incorporated by reference in its entirety.

GOVERNMENT RIGHTS

This invention was made with Government support under Contract Number DE-AC0676RLO1830 awarded by the U.S. Department of Energy. The Government has certain rights in the invention.

BACKGROUND

The present invention relates to electromagnetic radiation scanning/imaging techniques, and more particularly, but not exclusively, relates to detecting concealed objects carried by a person under clothing.

The detection of weapons, contraband, and other concealed objects is of significant interest at security checkpoints and the like. One approach utilizes a magnetometer to detect certain metallic objects. Unfortunately, this approach does not detect most organic polymer and composite materials that may be used to fabricate firearms, explosives, and other items that may pose a security threat.

In another approach, electromagnetic radiation within a selected wavelength range can be applied to provide images that can reveal objects hidden by clothing. However, this approach typically faces limitations regarding interrogation speed and/or image resolution that has made it undesirable for some applications—such as certain mass transit security checkpoints. Moreover, because these systems can provide detailed images of body parts that are ordinarily intended to be hidden by clothing, utilization of a human inspector can be embarrassing to the person being inspected, and may pose a concern that privacy rights are being violated. Thus, there is an ongoing demand for further contributions in this area of technology.

SUMMARY

One embodiment of the present invention is a unique technique to detect objects. Other embodiments include unique systems, devices, methods, and apparatus to determine if a person is concealing an object.

A further embodiment of the present invention is a technique that includes: detecting returned electromagnetic radiation having one or more frequencies in a range of about 200 Megahertz (MHz) to about 1 Terahertz (THz), from a surface beneath clothing of a person, establishing data from the returned electromagnetic radiation corresponding to intensity and depth along the surface, and adaptively processing the data to determine if a suspicious object is being carried by the person.

Another embodiment of the present invention is directed to a technique that includes: irradiating an interrogation region including a person carrying a concealed object, detecting electromagnetic radiation returned from the region in response to the irradiation, establishing data representative of a map of intensity of the electromagnetic radiation returned from the interrogation region and a map of depth along the interrogation region, and inputting the data into a neural network to detect the concealed object based on the maps of intensity and depth.

Still another embodiment of the present invention includes a technique to detect electromagnetic radiation returned from a subject, where the electromagnetic radiation includes one or more frequencies in a range of about 200 MHz to about 1 THz. Data is established that corresponds to intensity of electromagnetic radiation returned from the subject and depth difference along one or more surfaces of the subject. Adaptive processing is performed with the data to determine if a man-made object suspected to be at least one of contraband or a potential security threat is present as a function of the intensity and the depth difference. In one form, the subject undergoing interrogation is a person and the technique is performed to detect suspicious objects that might be concealed beneath clothing of the person. The adaptive processing can be performed with a neural network that evaluates each of several multipixel image portions. For each of a first set of inputs to the neural network, image pixel intensity is received in correspondence to the image pixels for a respective one of the image portions, and for each of a second set of inputs to the neural network, a depth difference pixel input is received in correspondence to the image pixels for the respective one of the image portions.

A further embodiment of the present invention includes an array operable to interrogate a person with electromagnetic radiation at one or more frequencies in a range of about 200 MHz to about 1 THz and a processing subsystem. This subsystem is coupled to the array and operates to define a neural network including a first set of inputs and a second set of inputs. The first set of inputs receives data corresponding to a map of returned electromagnetic radiation intensity along a surface beneath clothing of the person undergoing interrogation. The second set of inputs receives other data corresponding to a map of surface depth. The neural network evaluates if one or more objects suspected of being at least one of contraband and a potential security threat are being concealed by the person, and provides one or more corresponding outputs. This evaluation is performed as a function of the map of intensity and the map of depth.

Still a further embodiment includes a device carrying logic executable by one or more processors to analyze data corresponding to an image of a person obtained from electromagnetic radiation including one or more frequencies in a range of about 200 MHz to about 1 THz. This data represents a map of electromagnetic radiation intensity and a map of depth determined relative to the person. The logic is operable to execute an adaptive process with the data to evaluate if one or more objects of a suspicious nature are being concealed by the person as a function of the map of electromagnetic radiation intensity and the map of depth. In one form, the device includes a processor-readable memory and the logic is in the form of a number of instructions stored in the memory. In another form, the device includes one or more parts of a computer network and the logic is encoded in one or more signals for transmission over this network.

Accordingly, one object of the present invention is to provide a unique technique to detect items of interest.

Another object is to provide a unique system, method, device, or apparatus to determine if an object of interest is being concealed.

Other objects, embodiments, forms, features, advantages, aspects, and benefits of the present invention shall become apparent from the detailed description and drawings included herein.

DETAILED DESCRIPTION

Figure 1:
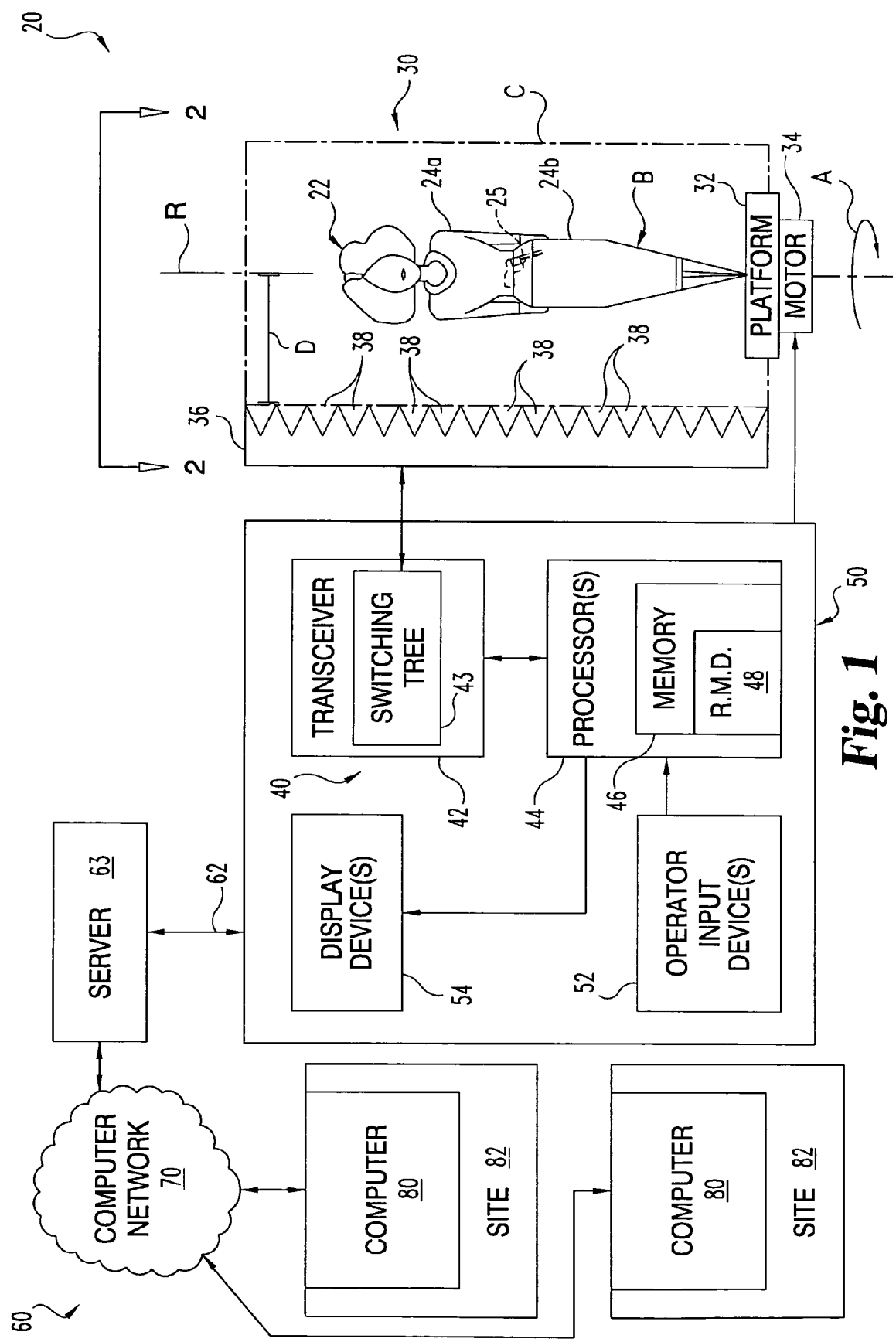
FIG. 1 is a partial, diagrammatic view of a security inspection system.

While the present invention may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 illustrates security inspection system 20 of one embodiment of the present invention. In operation, system 20 interrogates an animate or inanimate object by illuminating it with electromagnetic radiation in the 200 Megahertz (MHz) to 1 Terahertz (THz) frequency range and detecting the reflected radiation. Generally, the corresponding wavelengths range from several centimeters to a few micrometers. Certain natural and synthetic fibers are often transparent or semi-transparent to such frequencies/wavelengths, permitting the detection and/or imaging of surfaces positioned beneath such materials. When the subject of interrogation is a clothed individual, image information about portions of a person's body covered by clothing or garments can typically be obtained with system 20, as well as those portions that are not covered by clothing or garments. Further, image information relative to objects carried by a person beneath clothing can be provided with system 20 for metal and nonmetal object compositions commonly used for weapons and contraband.

As illustrated in FIG. 1, body B is in the form of person 22 presented for interrogation by system 20. Person 22 is portrayed in a typical manner, being at least partially covered by garments or clothing designated more specifically by reference numerals 24a and 24b. Clothing items 24a and 24b conceal object 25 shown in the form of a weapon in phantom. Person 22 is positioned in scanning/illumination portal 30 of system 20. Portal 30 is configured for placement at a security checkpoint where it is desired to detect weapons and/or contraband. Portal 30 includes platform 32 connected to motor 34. Platform 32 is arranged to support person 22 or such other object desired to be examined with system 20. Motor 34 is arranged to selectively rotate platform 32 about rotational axis R while person 22 is positioned thereon. For the orientation shown, axis R is approximately vertical, and person 22 is in a generally central position relative to axis R and platform 32. In one form, platform 32 can be comprised of a material, such as an organic thermoplastic or thermoset polymer, that permits interrogation in or beneath the soles of shoes where weapons can sometimes be hidden.

Figure 2:
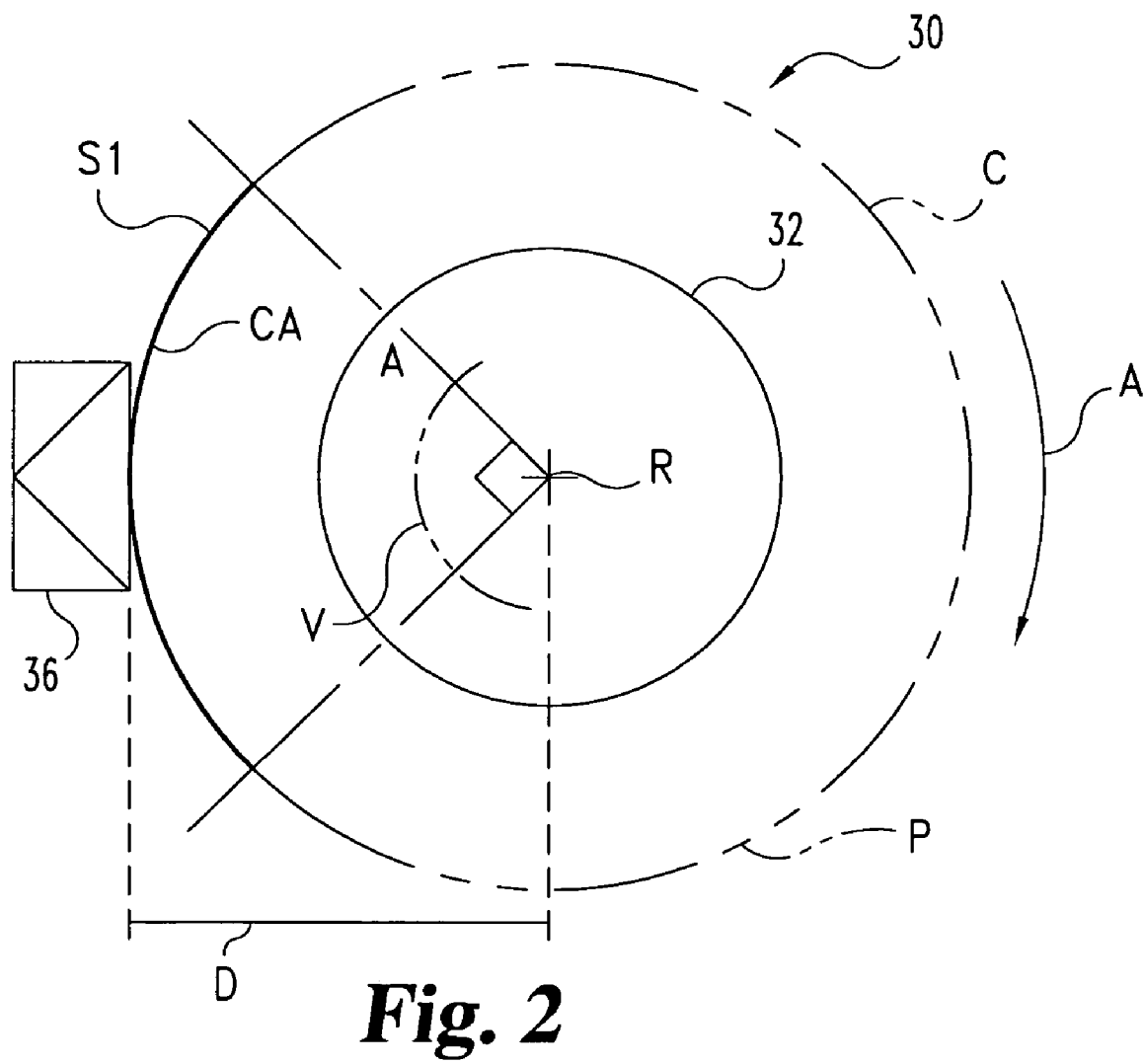
FIG. 2 is a partial, top view of the FIG. 1 system along the view line 2-2 shown in FIG. 1.

Portal 30 further includes multiple element-sensing array 36. Referring additionally to the partial top view of FIG. 2, the relationship of platform 32 to array 36 is further illustrated. Axis R is generally perpendicular to the view plane of FIG. 2 and is represented by crosshairs. As motor 34 causes platform 32 to rotate about axis R, array 36 circumscribes a generally circular pathway P about axis R. Circular pathway P corresponds to an imaginary cylinder C with radius D that corresponds to an interrogation region for portal 30. Radius D is the distance from axis R to array 36. In one preferred form, radius D is about 0.25 to about 3 meters. In a more preferred form, radius D is about 0.5 meters to 1.5 meters—corresponding to about a 1 meter to 3 meter diameter. Arrow A shown in FIGS. 1 and 2 represents the selective rotation of platform 32 about axis R.

Sensing array 36 includes a number of linearly arranged elements 38 only a few of which are schematically illustrated and specifically designated by reference numerals to preserve clarity. Elements 38 each operate to transmit or receive electromagnetic radiation within a selected bandwidth. Sensing array 36 is coupled to processing subsystem 40. Subsystem 40 includes transceiver 42 with switching tree 43 coupled to elements 38 of array 36. In one form, the position of array 36 relative to platform 32 is determined with one or more positional encoders (not shown) that are coupled to subsystem 40. In other forms, one or more different position tracking devices and/or positioning tracking techniques can be used.

Under the control of transceiver 42, individual elements 38 can be selectively activated with switching tree 43. Each element 38 is dedicated to transmission or reception. Elements 38 are arranged in two generally vertical columns arranged in a back-to-back relationship with one another. Elements 38 comprising one of the columns are dedicated to transmission and elements 38 comprising the other of the columns are dedicated to reception. The number of elements 38 in each column is in a range of about 32 to about 2000 elements and spans a vertical distance of about 2 to 2.5 meters along axis R; however, in other embodiments, a different vertical span and/or number of elements can be utilized. Transceiver 42 can control switching tree 43 to irradiate body B with only one element 38 of the transmitting column at a time and simultaneously receive with one or more elements 38 of the receiving column. Transceiver 42 includes logic to direct successive activation of each element 38 of the transmitting column and the corresponding one or more elements 38 of the receiving column to provide a scan of a portion of person 22 along a vertical direction with array 36. The corresponding "down range" or "time-of-flight" information can be used to provide positional data about a corresponding portion of person 22 under interrogation. Further information about such arrangements is provided in commonly owned U.S. Pat. No. 5,859,609, which is hereby incorporated by reference.

In a preferred embodiment, transceiver 42 and elements 38 of array 36 are of a form suitable to transmit and/or receive electromagnetic radiation selected from the range of about one Gigahertz to about one Terahertz (about 1 GHz to about 1 THz), which corresponds to a free space electromagnetic radiation wavelength range of about 0.3 meter (m) to about 300 micrometers (μm). In another preferred embodiment, an impulse transceiver arrangement is utilized that generates frequencies in a range of about 200 MHz to about 15 GHz depending on the impulse width, which corresponds to a free space electromagnetic radiation wavelength range of about 1.5 m to about 0.02 m. In a more preferred embodiment, the frequency range is about 1 GHz to about 300 GHz with a corresponding free space wavelength range of about 0.3 meter to about 1 millimeter (mm). In a most preferred embodiment, the frequency range is about 5 GHz to about 110 GHz with a corresponding free space wavelength range of about 0.06 m to about 2.7 mm.

The transmission pathway for a given element 38 of the transmitting column can be selected to be about the same length as the transmission pathway for the corresponding element(s) 38 of the receiving column to simplify calibration. Nonetheless, in other embodiments, the transmission/reception arrangement can differ. For example, in one alternative embodiment, one or more elements 38 are used for both transmission and reception. In another alternative embodiment, a mixture of both approaches is utilized. Typically, the signals received from array 36 are downshifted in frequency and converted into a processible format through the application of standard techniques. In one form, transceiver 42 is of a bi-static heterodyne Frequency Modulated Continuous Wave (FM/CW) type like that described in U.S. Pat. No. 5,859,609 (incorporated by reference herein). Commonly owned U.S. Pat. Nos. 5,557,283 and 5,455,590, each of which are incorporated by reference herein, provide several nonlimiting examples of other transceiver arrangements. In still other embodiments, a mixture of different transceiver/sensing element configurations with overlapping or nonoverlapping frequency ranges can be utilized that may include one or more of the impulse type, monostatic homodyne type, bi-static heterodyne type, and/or such other type as would occur to those skilled in the art.

Transceiver 42 provides the data corresponding to the array signals to one or more processors 44 of subsystem 40. Processor(s) 44 can each be comprised of one or more components of any type suitable to process the data received from transceiver 42, including digital circuitry, analog circuitry, or a combination of both. Processor(s) 44 can be of a programmable type; a dedicated, hardwired state machine; or a combination of these. For a multiple processor form; distributed, pipelined, and/or parallel processing can be utilized as appropriate.

Memory 46 is included with processor(s) 44. Memory 46 can be of a solid-state variety, electromagnetic variety, optical variety, or a combination of these forms. Furthermore, memory 46 and can be volatile, nonvolatile, or a mixture of these types. Memory 46 can be at least partially integrated with processor(s) 44. Removable Memory Device (R.M.D.) 48 is also included with processor(s) 44. R.M.D. 48 can be a floppy disc, cartridge, or tape form of removable electromagnetic recording media; an optical disc, such as a CD or DVD type; an electrically reprogrammable solid-state type of nonvolatile memory, and/or such different variety as would occur to those skilled in the art. In still other embodiments, R.M.D. 48 is absent.

Subsystem 40 is coupled to motor 34 to selectively control the rotation of platform 32 with processor(s) 44 and/or transceiver 42. Subsystem 40 is housed in a monitoring/control station 50 that also includes one or more operator input devices 52 and one or more display devices 54. Operator input device(s) 50 can include a keyboard, mouse or other pointing device, a voice recognition input subsystem, and/or a different arrangement as would occur to those skilled in the art. Operator display device(s) 52 can be of a Cathode Ray Tube (CRT) type, Liquid Crystal Display (LCD) type, plasma type, Organic Light Emitting Diode (OLED) type, or such different type as would occur to those skilled in the art. Station 50 is arranged to be controlled by one ore more security point operators responsible for the operation of system 20 as further described hereinafter.

System 20 further includes communication subsystem 60 coupled to subsystem 40 by communication link 62. Subsystem 60 includes network server 63 coupled to computer network 70. Computer network 70 can be provided in the form of a Local Area Network (LAN), a Municipal Area Network (MAN), and/or a Wide Area Network (WAN) of either a private type or publicly accessible type, such as the internet. Link 62 can be provided by such a network or be of a dedicated communication channel variety. Server 63 can be remotely located relative to subsystem 40. Indeed, in one embodiment, server 63 is coupled to a number of remotely located subsystems 40 with corresponding portals 30. In still other embodiments, more than one server 63 can be coupled to a common portal 30 and subsystem 40 arrangement. Alternatively or additionally, server 63 can be an integral part of subsystem 40. For yet other embodiments, server 63, network 70, and sites 80 are absent. Indeed, R.M.D. 48 can be used to alternatively or additionally transfer data between subsystem 40 and other computing/processing devices.

Server 63 is operable to communicate over network 70. Computer network 70 communicatively couples a number of sites 80 together. Each site 80 includes computer 82 arranged to communicatively interface with computer network 70. Each computer 82 includes one or more operator input device(s) 50 and one or more operator output device(s) 52 as previously described for subsystem 40, that are not shown to preserve clarity. Device(s) 50 and 52 at each site 80 selectively provide an operator input and output (I/O) capability. Computer 82 can be in the form of another subsystem 40, a personal computer or computer workstation, another computer server, Personal Digital Assistant (PDA), and/or a different configuration as would occur to those skilled in the art. While only two sites 80 are illustrated to preserve clarity, it should be understood that more or fewer can be coupled via computer network 70.

Collectively, server 63, computer network 70, and sites 80 provide an arrangement to remotely communicate with station 50. The interconnection of these components can be hardwired, wireless, or a combination of both. In lieu of or in addition to network 70, one or more of sites 80 and server 63 could be coupled by dedicated cabling or the like. Communication over network 70 can be used to monitor performance of station 50, update software associated with subsystem 40, remotely operate station 50 or portal 30, and/or share data pertinent to the recognition of suspicious objects with system 20 as will be more fully described hereinafter. In one such arrangement, one or more of sites 80 are configured as a repository for data pertinent to security screening with system 20.

Figure 3:
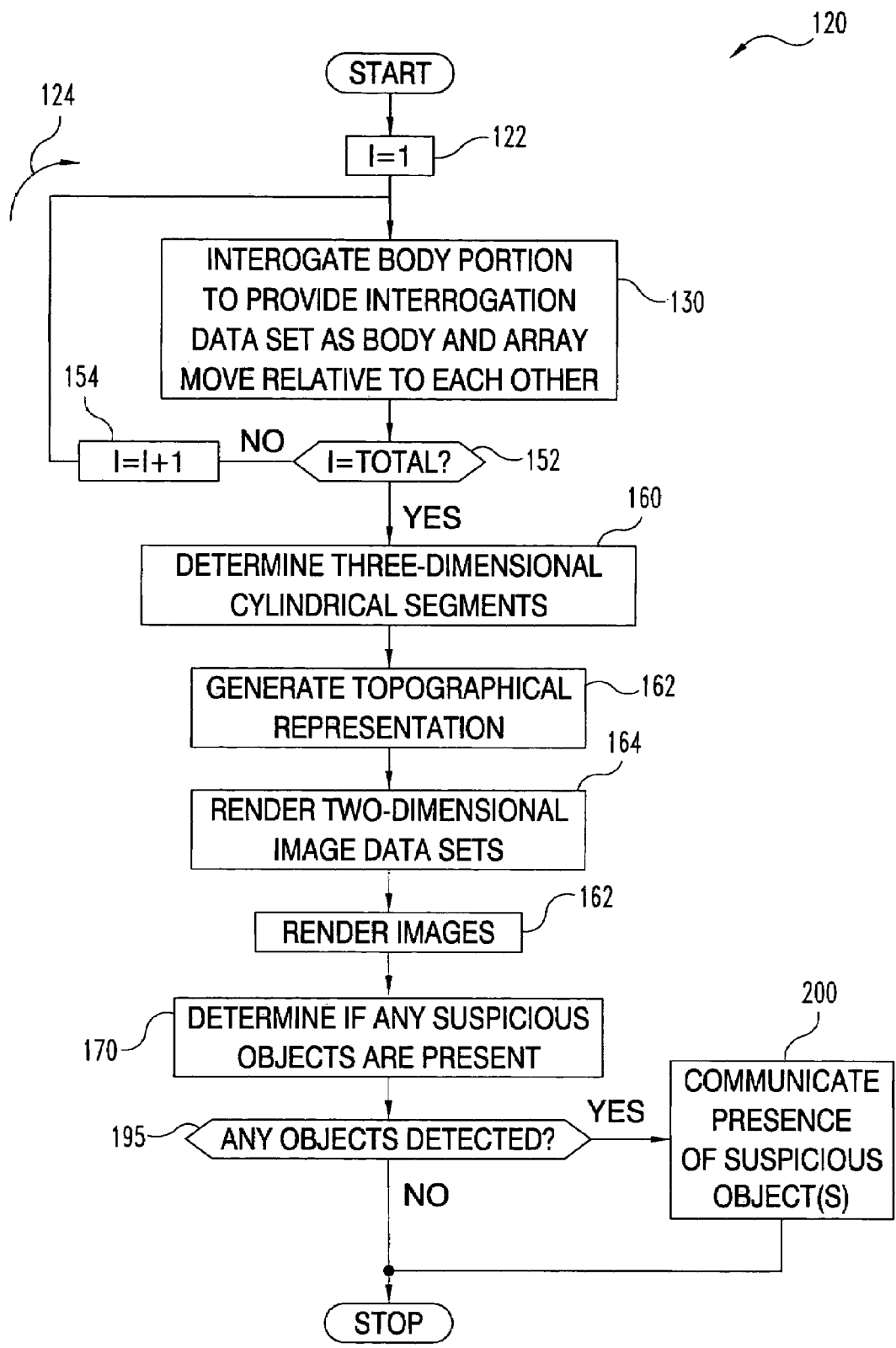
FIGS. 3 and 4 are flowcharts illustrating one procedure for operating the system of FIG. 1.

Referring additionally to the flowchart of FIG. 3, one mode of operating system 20 is illustrated as procedure 120. Procedure 120 is performed with system 20 to provide image information representative of person 22 carrying object 25. Procedure 120 begins with operation 121. In operation 121, person 22 enters portal 30 at a security checkpoint to be screened for weapons, contraband, and/or other items/materials. Procedure 120 proceeds to initialization operation 122 that sets interrogation index "I" to one (I=1). From operation 122, procedure 120 enters interrogation loop 124 beginning with interrogation routine 130. Interrogation routine 130 interrogates a portion of person 22 within a field of view of array 36 as person 22 rotates on platform 32. Index I is an integer index to the number of different interrogation routines 130 performed as part of procedure 120.

Figure 4:
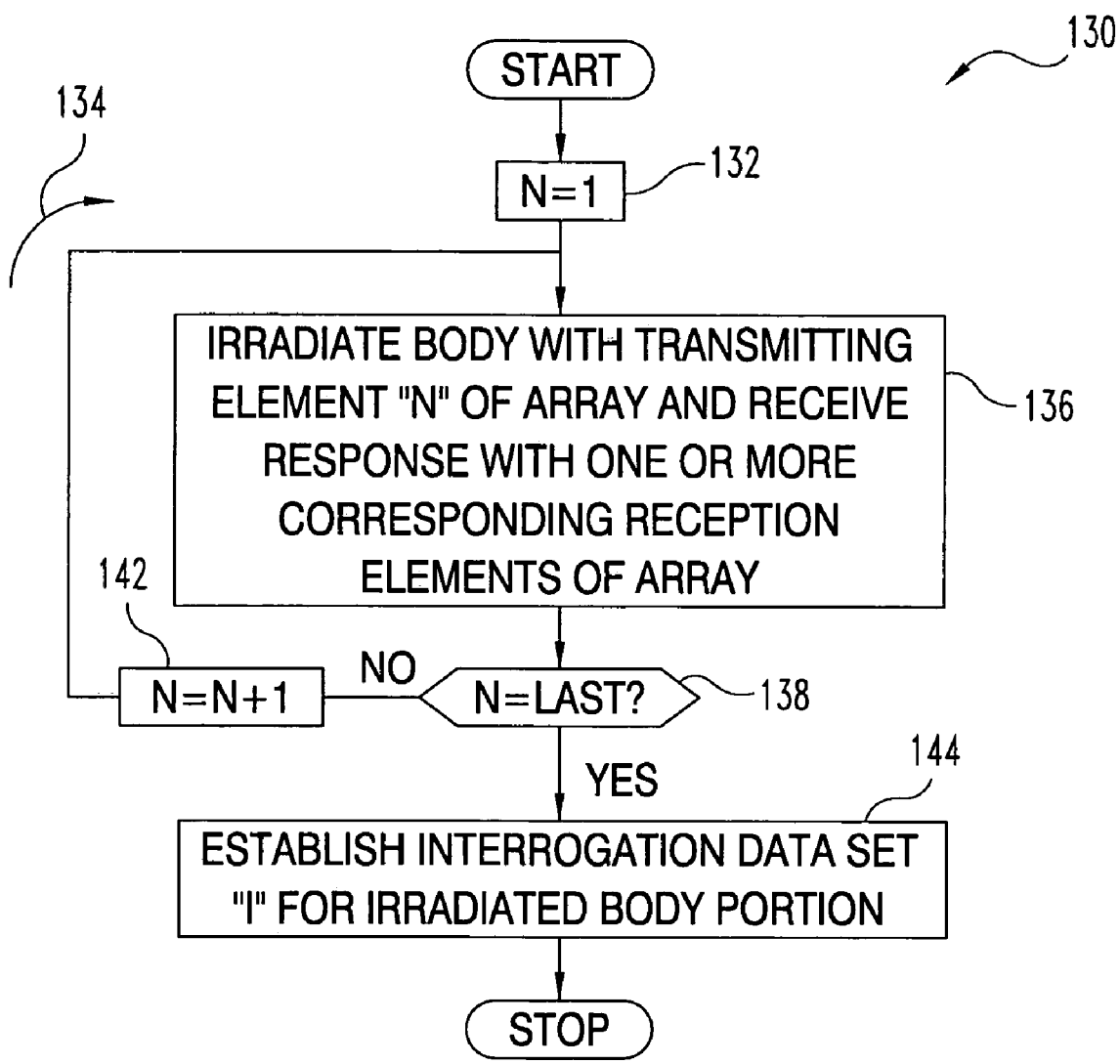

Referring to FIG. 4, interrogation routine 130 is further illustrated. Routine 130 begins with initialization operation 132 in which transmission index N is set to one (N=1). From operation 132, element sequencing loop 134 is entered, beginning with transmission/reception operation 136. Index N is an integer index to the number of transmission/reception operations 136 performed during routine 130. In operation 136, a portion of person 22 in the field of view of a transmitting element number "N" of array 36 is irradiated with electromagnetic radiation and one or more corresponding reception elements collect the reflected electromagnetic radiation in response to the transmission. The transmitting and reception elements are selected by logic of transceiver 42 with switching tree 43 as previously described. From operation 136, routine 130 proceeds to conditional 138, which tests whether transmitting element number "N" is the last element needed to transmit (N=LAST?); where LAST is the total number of the transmitting elements to be activated by transceiver 42.

In one form, for each execution of routine 130, transmitting element "N" sweeps through a selected frequency range twice, and the corresponding backscatter information for each of the two sweeps is received with a different reception element. The transmitting elements can be staggered relative to the reception elements such that transmitting element N aligns with a point between the two reception elements along a common axis of the array. U.S. Pat. No. 5,557,283 (incorporated by reference) describes an example of this arrangement of transmitting and reception elements. In other forms, a different technique can be utilized involving more or fewer sweeps, different types of sweeps, and/or different transmitting/reception orientations and numbers.

If the test of conditional 138 is negative (N<LAST), then increment operation 142 is performed, incrementing N by one (N=N+1). Loop 134 returns from operation 142 to transmission/reception operation 136 for execution with the transmitting/receiving subset of elements 38 corresponding to the new, incremented value of N from operation 142. In this manner, elements 38 are activated in a vertical path along array 36 with transceiver 42 to provide data along a contiguous region of person 22.

The resolution of interrogation information obtained with transceiver 42 can be enhanced by linearly sweeping through a selected ultrawide frequency range during each operation 136. In one preferred form, transceiver 42 sweeps through a range of at least 10 GHz for each execution of operation 136. This sweep can occur, for example, over a range of about 10 GHz to about 20 GHz. In a more preferred form, transceiver 42 and elements 38 are arranged for a sweep range of 16 GHz. This sweep can occur, for example, over a range of about 24 GHz to about 40 GHz. In one most preferred form, the ultrawide sweep range is selected such that the range resolution is generally the same as the lateral resolution. For these forms, elements 38 are selected to be of a type with a frequency response suitable for the selected sweep range, including, but not limited to the taper slot or end-fire antenna type. In another form, the transmitter can sweep through a given frequency range (such as 10 GHz to 20 GHz) in a pseudo-random order—sometimes known as frequency hopping.

Loop 134 is repeated LAST number of times, sequencing through the desired transmitting/receiving elements 38 of array 36 under the control of transceiver 42. When the test of conditional 138 is true, the affirmative branch proceeds to data operation 144. Data resulting from the execution of operation 136 is provided by transceiver 42 to processor(s) 44. In data operation 144, an interrogation data set is established for the information gathered through the repeated execution of operation 136 from N=1 through N=LAST. This data set corresponds to the current value of integer index I and the portion illuminated during these executions. Initially, the interrogation data set can be accumulated and organized by transceiver 42, processor(s) 44 or both; and then stored in memory 46 for further processing by processor(s) 44 as described in connection with the remainder of procedure 120. From operation 144, routine 130 returns to the next stage of procedure 120.

Referring back to FIG. 3, procedure 120 continues with conditional 152 that tests whether the final value of index I has been reached (I=TOTAL?); where TOTAL is the total number of desired executions of loop 124 (and routine 130) for procedure 120. If the test of conditional 152 is negative (I<TOTAL), procedure 120 continues to increment operation 154 to increment index I by one (I=I+1). Loop 124 then returns to routine 130 for the next execution until I is incremented to be equal to TOTAL.

With the execution of loop 124 TOTAL number of times, TOTAL number of interrogation data sets are stored in memory 46. When the test of conditional 152 is true, procedure 120 continues with cylindrical segmentation operation 160. In operation 160, the interrogation data sets are processed with processor(s) 44 to generate a number of cylindrical image data sets that each correspond to an arc segment of cylinder C. Referring to FIG. 2, arc segment S1 subtends a viewing angle V of about 90 degrees with respect to person 22. Arc segment S1 defines a cylindrical aperture CA that extends along axis R. The image data set corresponding to arc segment S1 represents the three-dimensional surface of body B that is reflective with respect to the selected electromagnetic radiation, as if viewed through cylindrical aperture CA. In one convenient form, the image data set is defined in terms of cylindrical coordinates, although any three-dimensional coordinate system can be used. Each image data set is determined from the interrogation data gathered for the corresponding arc segment by processor(s) 44. Reference is made to commonly owned U.S. Pat. No. 5,859,609 (incorporated herein by reference) for further description about the determination of cylindrical image data.

Figure 5:
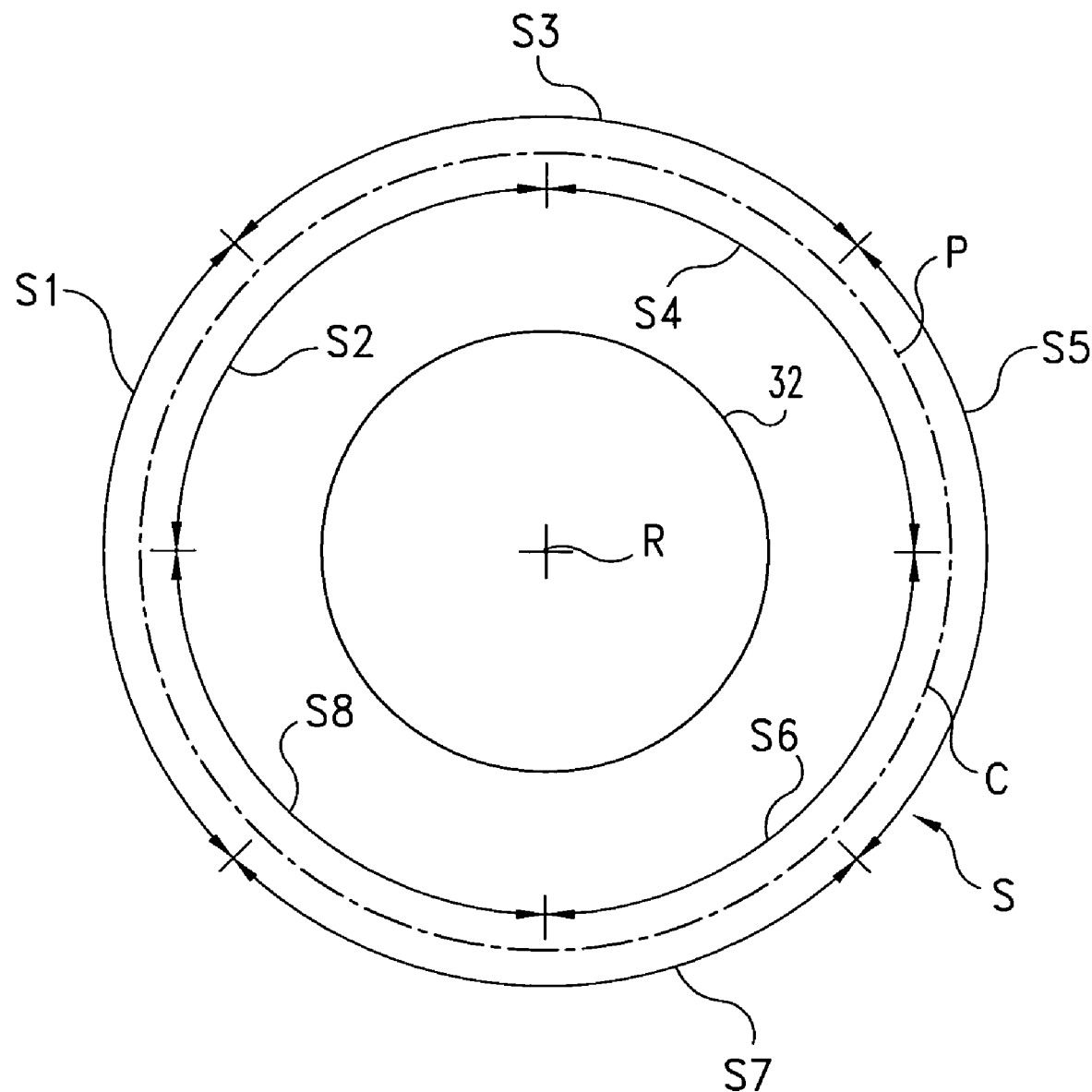
FIG. 5 is a schematic, top view of the system of FIG. 1 illustrating a number of overlapping arc segments.

During operation 160, cylindrical image data sets are determined for a number of arc segments about axis R that collectively circumscribe person 22. In FIG. 5, eight overlapping arc segments S1, S2, S3, S4, S5, S6, S7, and S8 (collectively segments S) are illustrated with respect the generally circular pathway P and corresponding cylinder C. Segments S1, S3, S5, and S7 are schematically represented by double-headed arrows slightly to the outside of path P and segments S2, S4, S6 and S8 are schematically represented by double-headed arrows slightly inside path P to preserve clarity. In FIG. 5, segments S each correspond to a viewing angle of about 90 degrees, and each one overlaps two others by about 45 degrees. It should be understood that each different segment S corresponds to a representation of a different portion of person 22. In other embodiments, the viewing angle can differ and/or may be nonuniform from one arc segment S to the next. Alternatively or additionally, overlap may be intermittent or absent.

Procedure 120 continues with mapping operation 162. In operation 162, the image data obtained for the circumscribing arc segments S are mapped by processor(s) 44 to a common surface for body B, which is turn defines a common volume of body B. Operation 162 can include reconciling a data point for one of the arc segments S for a given location that differs by a threshold amount from the data point of the same location for another of the arc segments S. In one embodiment, an averaging technique is used and intermediate data points are interpolated. In another embodiment, a weighting function is utilized that progressively reduces the contribution of a data point as the distance of that data point from the midpoint of the corresponding arc segment S increases. The cylindrical data sets are preferably combined incoherently (after computing the magnitude) to reduce undesirable phase interference in the images. Operation 162 provides a topographical representation of body B and the volume bounded by its surface(s) about axis R that are reflective with respect to the electromagnetic radiation used for the interrogations of routine 130.

Procedure 120 proceeds with operation 164. In operation 164, one or more image data sets are determined with processor(s) 44 from the topographic representation of body B provided by operation 162. These two-dimensional image data sets are rendered from the volumetric data for body B by performing a two-dimensional parallel ray projection from a desired viewing angle. Along each parallel ray, the intensity is attenuated in proportion to the data it encounters in the volumetric representation. After attenuation, the maximum voxel intensity is selected to represent an image pixel intensity for the corresponding ray. The attenuation factor is adjusted so that the back surface of the representation does not contribute to the rendering. Generally, the result is a two-dimensional map of image pixel intensity for each selected viewing angle. Besides intensity mapping, other characteristics of the interrogated subject can be mapped. For instance, the range from the interrogating array 36 to a selected region of a subject can be used to generate a characteristic image map. In one implementation, range can be used to generate a map of relative depth of the reflecting surface of the interrogated subject with respect to designated reference locations. Specifically, range (depth) can be determined from differences in the temporal delay between transmission and detection of returned electromagnetic energy. In one particular form, a "pixelated" image map of depth is provided from such range information with the reference locations ("depth pixels") being the same as the locations of the maximum intensity pixels for the intensity-based image map. This example is further considered in connection with routine 170a of FIG. 6 hereinafter.

The two-dimensional image (map) data sets can each be used to display a corresponding image with device(s) 52 as appropriate. In one embodiment, a number of two-dimensional images from different viewing angles are rendered from the volumetric representation in operation 164. These images can be presented in a selected sequence to provide an animation of body B. In one form, a sequence of about 32 to about 64 generally evenly spaced views about axis R are used to generate a rotating animation of body B about axis R. In other embodiments, data representative of one or more two-dimensional images/maps may be determined without the intermediate formation of a topographic representation. Systems utilizing a planar form of array to scan a subject are particularly suited to direct generation of two-dimensional image/map data, such as the system described, for instance, in connection with FIGS. 14 and 15 hereinafter. In still other embodiments, image display may only be partially shown, schematically registered, and/or dependent on the detection of a suspicious object as is more fully described next.

From operation 164, procedure 120 continues with the performance of object detection operation 170. In operation 170, a determination is made whether the person is carrying one or more objects of interest, such as those that may pose a threat to security. These objects may be completely or partially concealed by clothing of person 22. In one form, the determination is initially performed by inspection of one or more images rendered in operation 164. Alternatively or additionally, numerical processing of image data is performed to determine if one or more suspicious objects are being carried by person 22, such as concealed object 25 shown in FIG. 1. Nonlimiting examples of such numerical techniques are further described in connection with FIGS. 6-10 hereinafter. After operation 170, conditional 195 tests whether any suspicious objects were indicated. If the test of conditional 195 is negative (false), procedure 120 halts. If the test of conditional 195 is positive (true), procedures 120 continues with operation 200. In operation 200, the presence of suspicious objects is communicated to an operator.

This communication can include displaying an image of some or all of the subject associated with the suspect object as generated in operation 164. Visual and/or audible alert signals can be generated in operation 200 to focus the operator's attention on the person undergoing inspection and/or a corresponding image. Optionally, the suspect image features can be highlighted by a visual characteristic such as an identifying color, blinking/flashing or other intensity variation, and the like. Based on this display, an operator can determine if further inspection is warranted, if person 22 should be detained as a security risk, and the like. Additionally or alternatively, information pertaining to the classification and detection of the objects can be displayed in text or graphic form for operator consideration. As another option, different views of the person and/or suspect image regions can be displayed simultaneously. In further variations, an operator can switch between different views and/or can zoom-in or zoom-out to change relative size of an image being displayed using input device(s) 52. In still other embodiments, false alarms can be used to refine detection criteria as desired.

To hide/conceal body features to which a privacy objection might be made, the person's body can be displayed as a schematic body image, such as a silhouette, mannequin, wire-frame body, other gender-neutral representation, and/or as a visible light range photograph or video representation of the person. On such body representations, an correspondingly located overlay of any suspicious objects can be displayed for operator viewing. Alternatively or additionally, privacy concerns can be addressed by inspecting cross-sectional images taken along the height of person 22 to at least partially evaluate whether a suspicious object is potentially being carried. One approach to cross-sectional imaging is further described in U.S. Pat. No. 6,507,309 (incorporated by reference), which is, instead, directed to gathering dimensional information about the sectioned region, such as its circumference. Other inventive aspects of sectional views are further described in connection with the experimental examples illustrated in connection with FIG. 13 hereinafter.

To further reduce the quantity of operator inspected images that could be subject to a privacy complaint, numerical processing in operation 170 can be used to initially identify which images are to be presented to an operator—specifically only those for which such processing has indicated the presence of a suspicious object. Accordingly, an operator only reviews images that are indicated to show one or more objects of interest, such as a weapon or contraband, and privacy concerns are at the very least reasonably reduced if not completely eliminated. In still other embodiments, display of images of the body beneath clothing may be conditionally or unconditionally acceptable, or may be altogether absent. Alternatively or additionally, the information gathered with subsystem 40 is sent via computer network 64 to one or more remote sites 80. Sites 80 can perform some or all of the data processing of procedure 120 in lieu of processor(s) 44. In one process, a clothed individual is nonintrusively scanned by portal 30 and the image information is sent via server 63 and network 70 to a designated computer 82. Alternatively or additionally, background information about a person carrying an object of interest can be accessed via server 63 and network 70.

After execution of operation 200, procedure 120 terminates. Also, if conditional 195 is negative, procedure 120 terminates, bypassing operation 200. It should be understood that procedure 120 can be repeated for each person passing through a given security checkpoint and/or can be repeated multiple times for a given person if results appear to be ambiguous.

Numerical processing routines 170a and 170b are further described in connection with FIGS. 6-10. Routines 170a and/or 170b can be implemented with system 20 in the same manner as procedure 120 or as a part thereof. With respect to routine 170a in particular, it has been discovered that intensity and depth can be used to discern made-made objects carried by a human subject. Generally, man-made objects of the type used as a weapon or contraband often have flat surfaces and sharp edges that can be discriminated from the typically smoother, curved surfaces of a human subject based on intensity and depth mapping provided with reflected/returned electromagnetic energy having one or more frequencies in the 200 MHz to 1 THz range. Routine 170a is one embodiment implementing this discovery.

Figure 6:
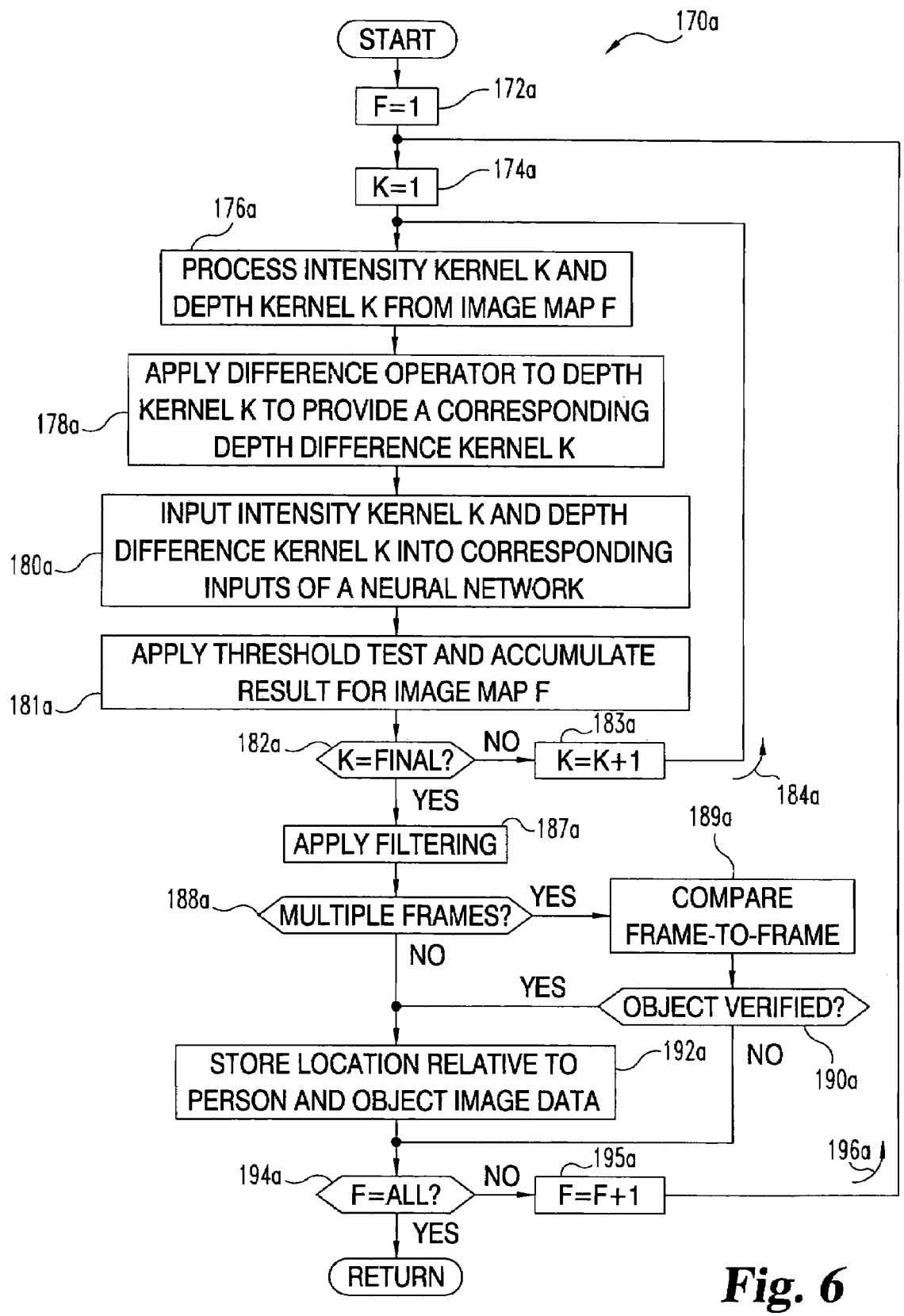
FIG. 6 is a flowchart of one type of object detection routine.

In routine 170a, numerical processing of image data is performed in operation 170 in lieu or in addition to any other detection approach to determine if one or more suspicious objects are present—such as a weapon and/or contraband being carried beneath clothing of person 22. Referring to FIG. 6, routine 170a is shown in flowchart form. Routine 170a begins by setting image counter F to one (F=1) in operation 172a. Counter F indexes the adjacent images from operation 162 for processing in routine 170a. Initially, routine 170a generates two different two-dimensional image data maps of the type previously described in connection with operation 164 of procedure 120. These are: (a) a two-dimensional map derived from the topographical representation based on maximum pixel intensity (an intensity map) and (b) a two-dimensional map based on relative depth of the reflecting surface as determined from range information (a depth map).

For each image map F, routine 170a selects a number of smaller image portions to each be separately evaluated in a kernel operation indexed by counter K. Each image map kernel K corresponds to a group of image pixels from the intensity map and the depth map. This group of image pixels have the same relative locations in each of the two maps. In operation 174a, kernel index counter K is set to one (K=1). From operation 174a, routine 170a proceeds to operation 176a. In operation 176a, kernel K of current image F is selected for processing.

From operation 176a, routine 170a continues with operation 178a. In operation 178a, a difference operator is applied to the depth map for kernel K to provide a corresponding depth difference map. Specifically, this difference operator approximates a derivative of the two-dimensional depth map by using a differencing operation. In other forms, a differential operator could be similarly utilized. As used herein "depth difference" for a map or image is intended to refer to the result of either a continuous differential and/or discrete differencing operation applied to a depth map. Accordingly, it should be understood that an operation performed as a function of depth encompasses, but is not limited to, a more specific operation performed as a function depth difference.

From operation 178a, routine 170a proceeds to operation 180a. In operation 180a, input from the intensity map for kernel K and depth difference map for kernel K are provided to corresponding inputs of a neural network for adaptive processing. In one form, the extracted features are input into a multilayer perceptron form of neural network. The network is configured for object identification through a repetitive training process, such as a back propagation of error algorithm. In still other embodiments, a different type of neural network and/or training technique may be additionally or alternatively utilized. In yet further embodiments, a different type of adaptive processing technique can be utilized in addition to or as an alternative to a neural network, such as fuzzy logic, an operator-assisted expert learning system, or the like. Further, nonadaptive processing can be alternatively or additional utilized. Also, it should be appreciated that some or all the desired depth difference information can be performed intrinsic to operation 180a in lieu of operation 178a based on input of the direct depth variation map information and/or a different function dependent on depth can be input to the neural network using techniques known to those skilled in the art. Alternatively or additionally, a different function dependent on intensity image information can be input to the neural network in lieu of some or all of the direct intensity map information using techniques known to those skilled in the art.

In one particular form, a kernel size of 7-by-7 pixels is utilized for both the depth and intensity data. For this arrangement, one form of perceptron neural network that has been utilized included four layers with 98 inputs (7×7=49 pixels from each of the two input sources to provide 49×2=98 inputs total). This network included 140 neurons in the first hidden layer, 25 neurons in the second hidden layer, and two outputs. These outputs represent the classes: (1)

identifiable as a man-made object and (2) not identifiable as a man-made object. Other classes, such as one corresponding to the identification of a "human" attribute could be included. In the experiment performed, the neural network simultaneously examined both of the 49-pixel areas of intensity and depth difference mapping to decide if there was a man-made object within the kernel window. For each kernel K processed, the outputs are compared to a threshold value to provide a discrete result in operation 181a. This threshold can be manually and/or dynamically adjusted based on false alarm rate, detection rate, or the like.

From operation 180a, routine 170a proceeds to conditional 182a which tests whether kernel K is the last (FINAL) kernel of the given image requiring analysis. If not, the negative (false) branch from conditional 182a proceeds to operator 183a to increment K (K=K+1). From operation 183a, routine 170a returns to operation 176a via loop 184a to process the next intensity kernel K and depth kernel K from image F. For each execution of loop 184a, kernel K shifts to a different group of pixels; however, one or more pixels may be included in two or more kernels K, such that there is a degree of overlap. In other embodiments, one or more pixels may be skipped from one kernel K to the next kernel K. In still other embodiments, the pixel composition of kernel K may be dependent on the nature of the neural network output. In one particular example, the degree of overlap between kernels K is increased when a suspicious object is indicated by adaptive processing and/or selected kernel processing is reconfigured to process previously skipped pixels proximate to any pixels indicating such an object.

As different kernels K of the two maps are processed by the neural network in loop 184a, threshold output results are accumulated in operation 181a to provide a corresponding adaptively processed image map with a discrete indication of any suspicious man-made objects detected. This image map corresponds to the output for each kernel K and correspondingly may have a resolution dependent of the technique(s) used to define the kernels. Also, it should be understood that while loop 184a processes one kernel K at a time, in other embodiments two or more kernels could be processed in parallel and/or different kernel sizes or configurations could be used. If the test of conditional 182a indicates the final kernel K has been processed for image F, then the affirmative (true) branch from conditional 182 proceeds to operation 187a.

In operation 187a, one or more filters are applied to remove false alarms and/or false negatives from the resulting adaptively processed image provided for image F by the repetitive processing of different kernels K in loop 184a. In one form, a median filter is applied that replaces each pixel with the median value of its neighbors to generally remove single outlying pixels potentially produced by noise. Alternatively or additionally, one or more morphological filters may be utilized to change the structure of an image. Such morphological filters can include a dilation and/or erosion type. As used herein a "dilation filter" thickens an object by filling void spaces, and an "erosion filter" thins an object by reducing stray pixels. In one particular experimental example, a series of three to four filters was utilized with different settings to produce first an erosion filtering operation and then a dilation filtering operation.

From operation 187a, conditional 188a is encountered which tests whether multiple frames are available for the particular type of imaging technique. Notably, multiple frames are generally produced by procedure 120, providing an affirmative (true) result for conditional 188a. From this affirmative branch, operation 189a is encountered which compares suspected object locations from one frame to the next to provide a measure of object detection validation if a suspicious a man-made object is found in adjacent frames. If the frame-to-frame check verifies the detected object per conditional 190a, then routine 170a proceeds to operation 192a from the positive (true) branch of conditional 190a. In operation 192, the location of the suspicious object is stored relative to the image map of person 22 for subsequent processing in operation 200 of procedure 120. If the frame-to-frame check is inconsistent, then the test of conditional 190a is negative (false), and routine 170a proceeds to conditional 194a. Further, for embodiments in which multiple frames are not available, and/or for which a frame-to-frame check is not desired, the test of conditional 188a is negative (false), resulting in routine 170a proceeding unconditionally to operation 192a.

Conditional 194a tests whether all of the images F have been processed. If the test of conditional 194a is negative (false), then the index F is incremented (F=F+1) in operation 195a and routine 170a returns to operation 174a via loop 196a to repeat the kernel-by-kernel analysis of the next image F. If all of the images have been analyzed, then the affirmative branch of conditional 194a is encountered and routine 170a halts, returning to its calling routine (such as procedure 120).

Figure 7:
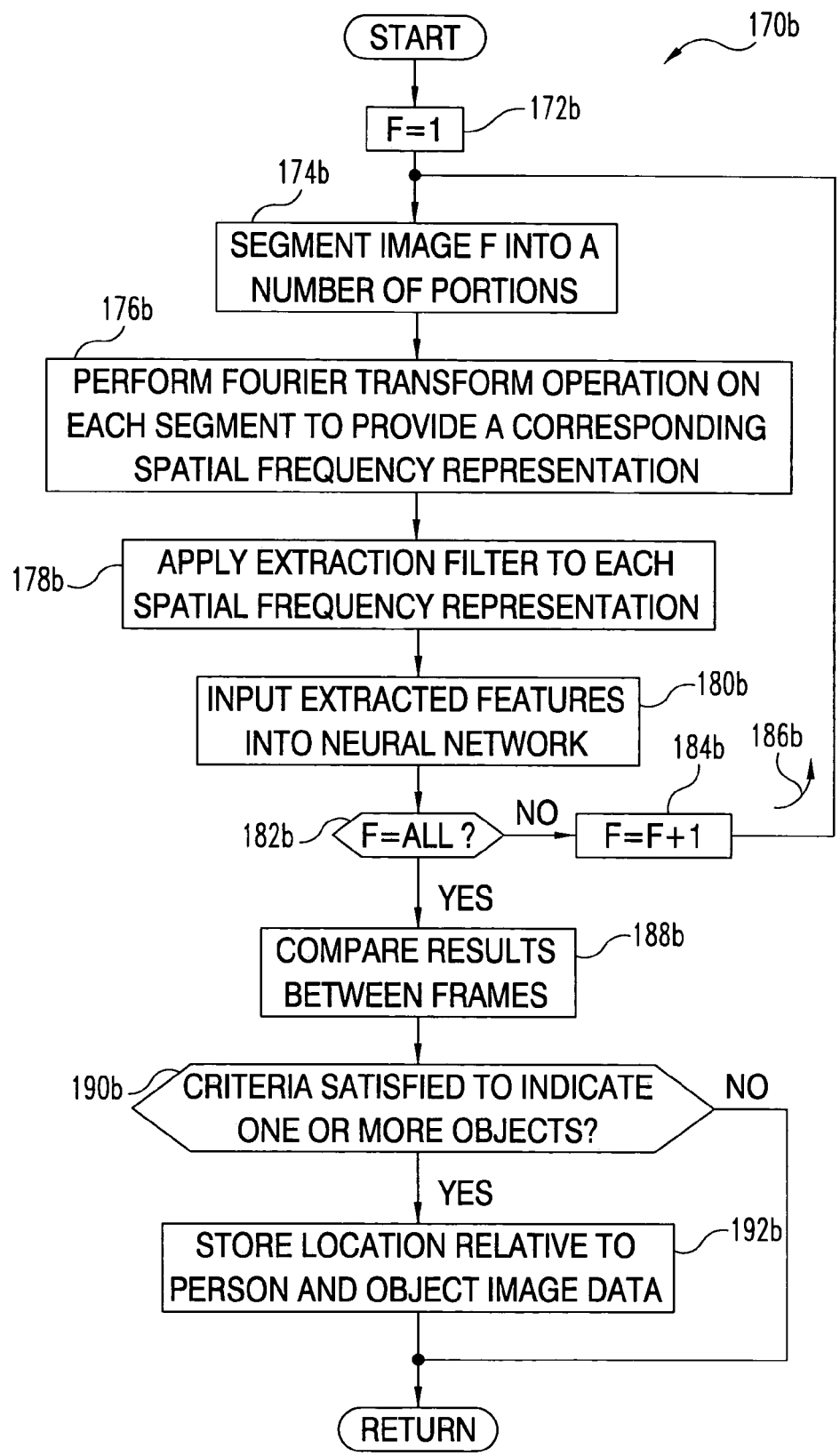
FIG. 7 is a flowchart of another type of object detection routine.

As an addition or alternative to routine 170a, numerical processing of image data in operation 170 can be performed in accordance with routine 170b to determine if one or more suspicious objects are present—such as a weapon and/or contraband being carried beneath clothing of person 22. Referring to FIG. 7, routine 170b is shown in flowchart form. Routine 170b begins by setting image counter F to 1 (F=1) in operation 172b. Counter F indexes the adjacent images from operation 164 for processing in routine 170b. From operation 172b, routine 170b proceeds to operation 174b. In operation 174b, the current image F is segmented or broken-up into a number of portions.

Figure 8:
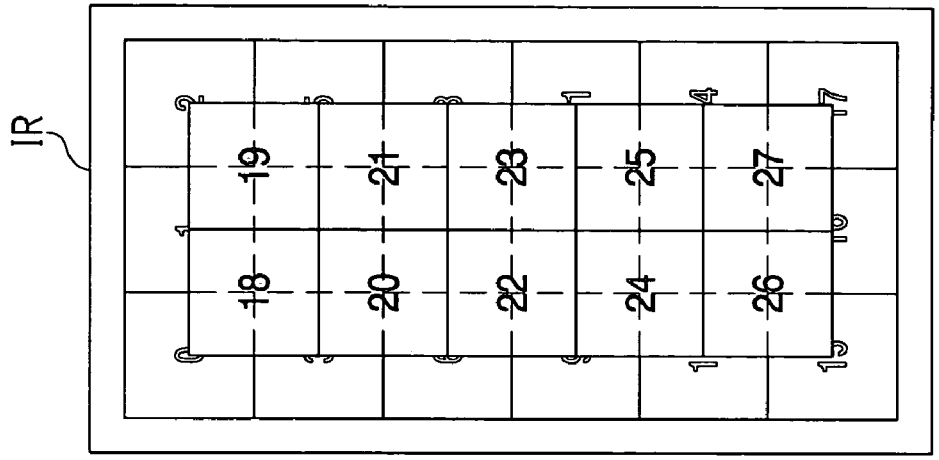
FIG. 8 is a diagram illustrating segmentation of an image into overlapping rectangular portions for use in the routine of FIG. 7.
Figure 8:
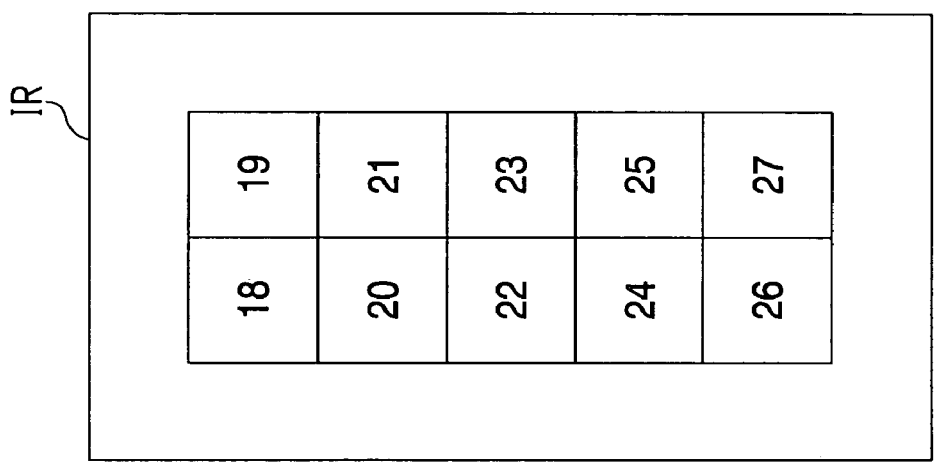
Figure 8:
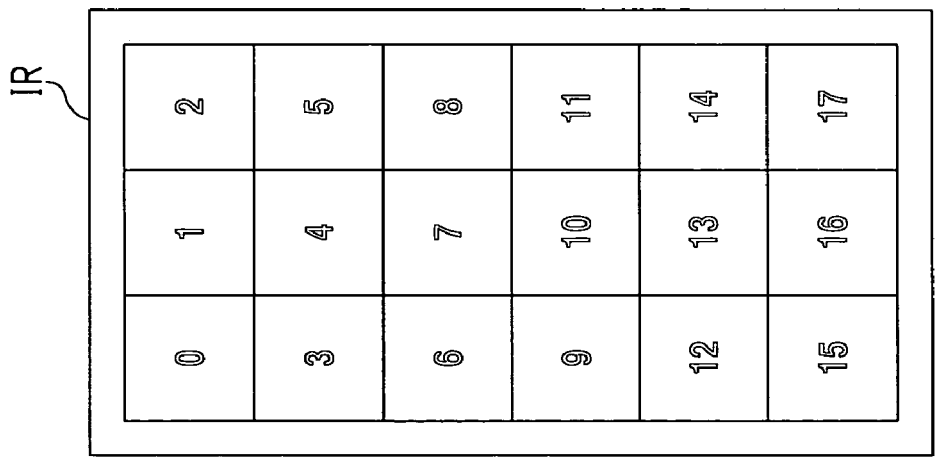

Referring additionally to FIG. 8, a rectangular image region IR is illustrated in three adjacent fields. In the leftmost field, image region IR is segmented into a first set, Set 1, of image portions numbered 0-17. In the middle field, image region IR is segmented into a second set, Set 2, of image portions numbered 18-27. Image portions 0-17 overlap image portions 18-27 as illustrated in the combined set in the rightmost representation of image region IR in FIG. 8. In one embodiment, the size of a segment is selected to be large enough to contain most of the region necessary to indicate a common object type of interest, but not so large as to make it difficult to localize such an object. In one arrangement utilizing Ku-band electromagnetic radiation, a segment size of about 32 by 32 pixels was found to be desirable. Nonetheless, in other embodiments, other sizes, shapes, patterns, degrees of uniformity, and/or different attributes may be varied as would occur to those skilled in the art with or without overlapping portions.

Referring back to FIG. 7, routine 170b continues with operation 176b. In operation 176, image data for each segment undergoes a Fourier transformation into Fourier spatial frequency space. Operation 176b can be performed with subsystem 40 to provide a corresponding spatial frequency representation for each image segment. Typically, such a representation is complex-valued. It has been found that man-made objects often have a spatial frequency representation that typically has a higher percentage of upper spatial frequencies relative to natural objects, such as the human body. Also, spatial frequency representations for man-made objects tend to dominate in certain directions in a spatial frequency distribution over Fourier space. Such distinctions can be utilized to classify image portions suspected of revealing a man-made object.

Figure 9:
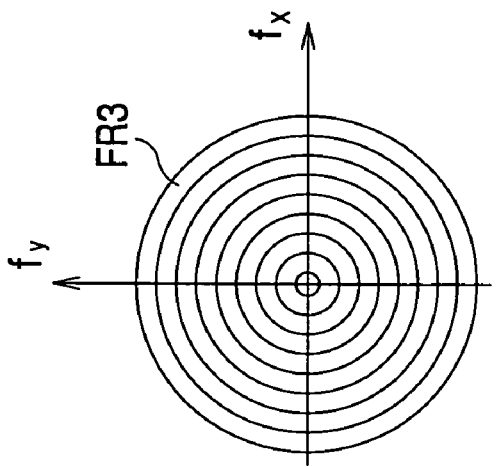
FIG. 9 is a diagram comparing three different types of feature extraction filters for use with the routine of FIG. 7.
Figure 9:
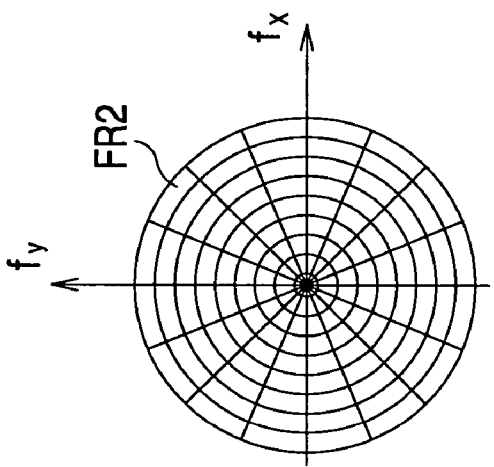
Figure 9:
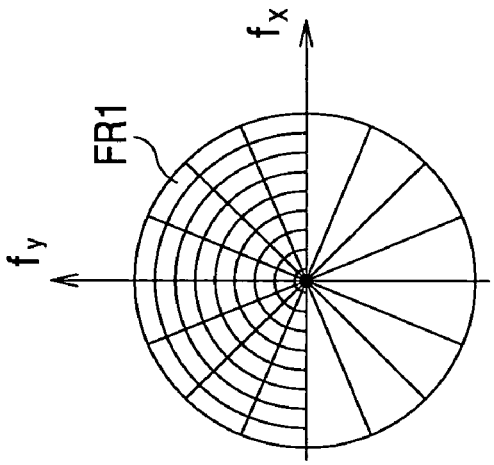

Because spatial frequency information of the type provided by a Fourier transform operation typically involves complex values, it is often desirable to simplify the data as part of the object detection procedure. In operation 178b, an extraction filter is applied to extract features from the spatial frequency representation that may be indicative of a man-made object. Referring additionally to FIG. 9, three different feature extractor filters FR1, FR2, and FR3 are illustrated in diagrammatic form relative to Fourier space. Feature extractor FR1 is of a ring-wedge configuration, including a half-plane of wedges and a half-plane of rings centered on the zeroth ($0^{th}$) frequency component in Fourier space. For this extractor, the wedges provide scale invariance and the rings provide rotational invariance. Extraction filter FR2 is of a sector configuration. By integrating spatial frequencies within each sector, a set of features representing angular and radial aspects of the corresponding image segment can be generated. While not invariant, extraction filter FR2 can be utilized to identify objects having preferred orientations and/or sizes. Extraction filter FR3 is of a ring configuration that is rotation invariant and so represents a segment based on a radial spatial frequency component. In operation 178b, one or more of these extraction filter types (FR1, FR2, FR3) can be applied and/or a different type of extraction filter may be utilized. In still other embodiments, extraction at this stage may be absent.

In operation 180b, features extracted during operation 178b are input into a neural network defined with subsystem 40. In one form, the extracted features are input into a multilayer perceptron form of neural network. The network is configured for object identification through a repetitive training process, such as a back propagation of error algorithm. In still other embodiments, a different type of neural network and/or training technique may be additionally or alternatively utilized. In yet further embodiments, a different type of adaptive processing technique can be utilized in addition to or as an alternative to a neural network, such as fuzzy logic, an operated-assisted expert learning system, or the like. Alternatively or additionally, nonadaptive processing can be utilized.

From operation 180b, routine 170b continues with conditional 182b which tests whether all the images have been processed in accordance with operations 174b-180b. If not, counter F is indexed (F=F+1) in operation 184b and loop 186b returns to operation 174b to process the next image. If conditional 182b is affirmative, routine 170b continues with operation 188b in which the results obtained from loop 186b for different image frames are compared to determine if they are consistent with one other. In one nonlimiting example with respect to arc segments S, the image results for arc segments S1 and S2 could be compared to each other to the extent they overlap (see FIG. 5). Likewise overlapping image results for arc segment pairs S2 and S3, S3 and S4, S4 and S5, S5 and S6, S6 and S7, S7 and S8, and S8 and S1 can be compared for consistency during operation 188b. In other embodiments, more or fewer frames and/or a different frame-to-frame comparison can be made. In yet other embodiments, there is no frame-to-frame comparison made at all.

From operation 188b, conditional 190b is encountered in which frame comparison results and/or one or more other desired detection threshold/criterion are tested to determine if any objects of interest are indicated. If such objects are indicated, then the relative location to the person and object image data is stored in operation 192b. If the test of conditional 190b is negative then routine 170b returns, bypassing operation 192b. It should be understood that the performance of any of operations 174b-180b and 188b, and/or conditional 190b can involve comparing processing results to one or more threshold valves or other criteria to determine if a corresponding image, image portion or representation, image feature, or the like indicates an object of interest. Any such criteria can be static or dynamic in nature. Dynamic criteria may be operator adjustable, adaptively machine adjusted, and/or selectively changed through a different technique as would occur to those skilled in the art. Referring back to FIG. 3, once routine 170b is completed, procedure 120 can proceed to conditional 195, and if one or more suspicious objects were detected, operation 200.

Figure 10:
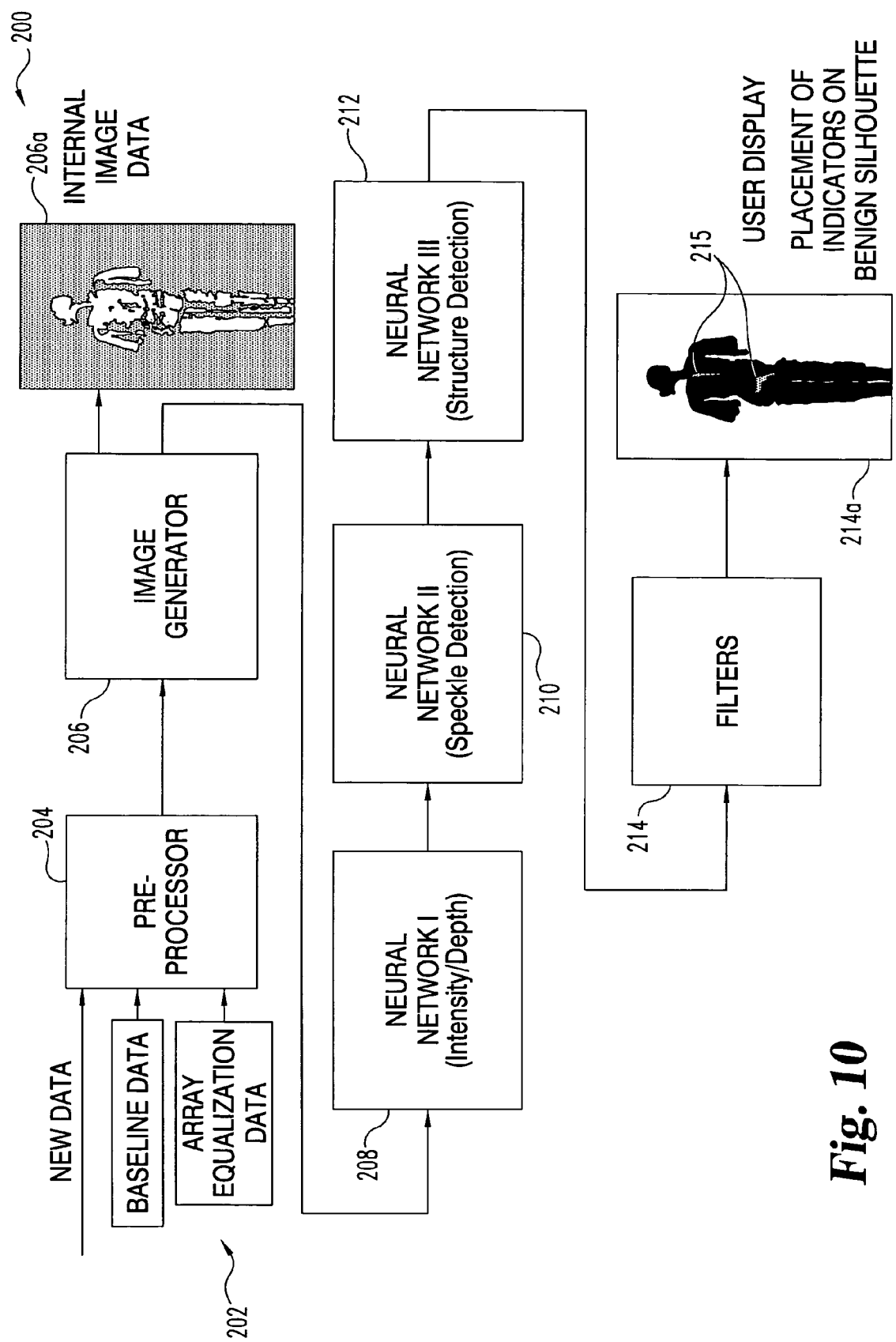
FIG. 10 is a schematic block diagram of an arrangement for detecting concealed objects that utilizes the system of FIG. 1 to execute the procedure of FIGS. 3 and 4 with both of the routines of FIGS. 6 and 7.

FIG. 10 illustrates object detection arrangement 200 in block diagram form. Arrangement 200 can be implemented with system 20. In system 200, new data, baseline data, and equalization data for a given transducer array is input into preprocessor 204 as generally designated by reference numeral 202. The output of preprocessor 204 is further provided to image generator 206 that can produce internal image data regarding the subject under interrogation. This internal image data is represented in a grayscale, computer-generated form as image 206a. It should be understood that this internal image data may not be displayed due to privacy concerns and/or may be presented in a manner that masks gender-based features, as previously described in connection with procedure 120.

The internal image data provided by generator 206 is further provided to neural network I, which is included in operator 208. Neural network I is configured to determine object presence based on intensity and depth difference information as described in connection with routine 170a. In one form, operator 208 is arranged to perform routine 170a previously described in connection with FIG. 6 to detect possible man-made objects or structural features. In addition to operator 208, the image data is further provided to neural network II which is included in operator 210. Operator 210 is arranged to detect speckling in an image that is sometimes indicative of certain types of dielectric materials, including certain types of explosives. Furthermore, the image data from generator 206 is provided to neural network III, which is included in operator 212. Operator 212 is directed to the detection of man-made structural features based on spatial frequency information. In one form, neural network 212 is arranged to perform routine 170b previously described in connection with FIGS. 7-9. The outputs of operators 208, 210, and/or 212 are provided to various filters 214, such as those described in connection with routines 170a and/or 170b to provide an output that indicates the presence of one or more suspicious objects. Visual representation(s) of object(s) can be overlaid on a gender-neutral silhouette display if detected. In one form, regions corresponding to such object(s) are shown in a contrasting color, tone, shade, or by other means, such as those previously described for procedure 120. Image 214a is a grayscale, computer-generated example of such an output. In image 214a, two suspect objects are indicated by a contrasting grayscale shade in regions 215.

It should be appreciated that arrangement 200 can be implemented with system 20 through various hardware and software techniques as previously described. Furthermore, while neural networks 208, 210, and 212 are shown in series, they may further be arranged in parallel or a series/parallel combination, as well as in a variety of other ways as would occur to those skilled in the art. Indeed, there are many other structural implementations and systems that can be used to implement procedure 120, routine 170a, routine 170b, and/or one or more operations of arrangement 200.

Referring back to system 20 of FIG. 1, transceiver 42 and processor(s) 44 include logic that can be arranged to perform the various operations described herein, including those described in connection procedure 120, routine 170a, routine 170b, arrangement 200, and/or variations of these. This logic can be in the form of software programming instructions, firmware, and/or of a hardwired form, just to name a few. Furthermore such logic can be in the form of one or more signals carried with memory 46, R.M.D. 48, and/or one or more parts of computer network 76. In one example, logic signals to perform one or more operations are transmitted to/from processor(s) 44 via network 70. Alternatively or additionally, programming for processor(s) 44 is transported or disseminated through R.M.D. 48 and/or one or more other storage devices. Nonlimiting examples of other systems that can implement the operations of procedure 120, routine 170a, routine 170b, and/or arrangement 200 (including associated logic) include those described in connection with FIGS. 11-18 as follows.

Figure 11:
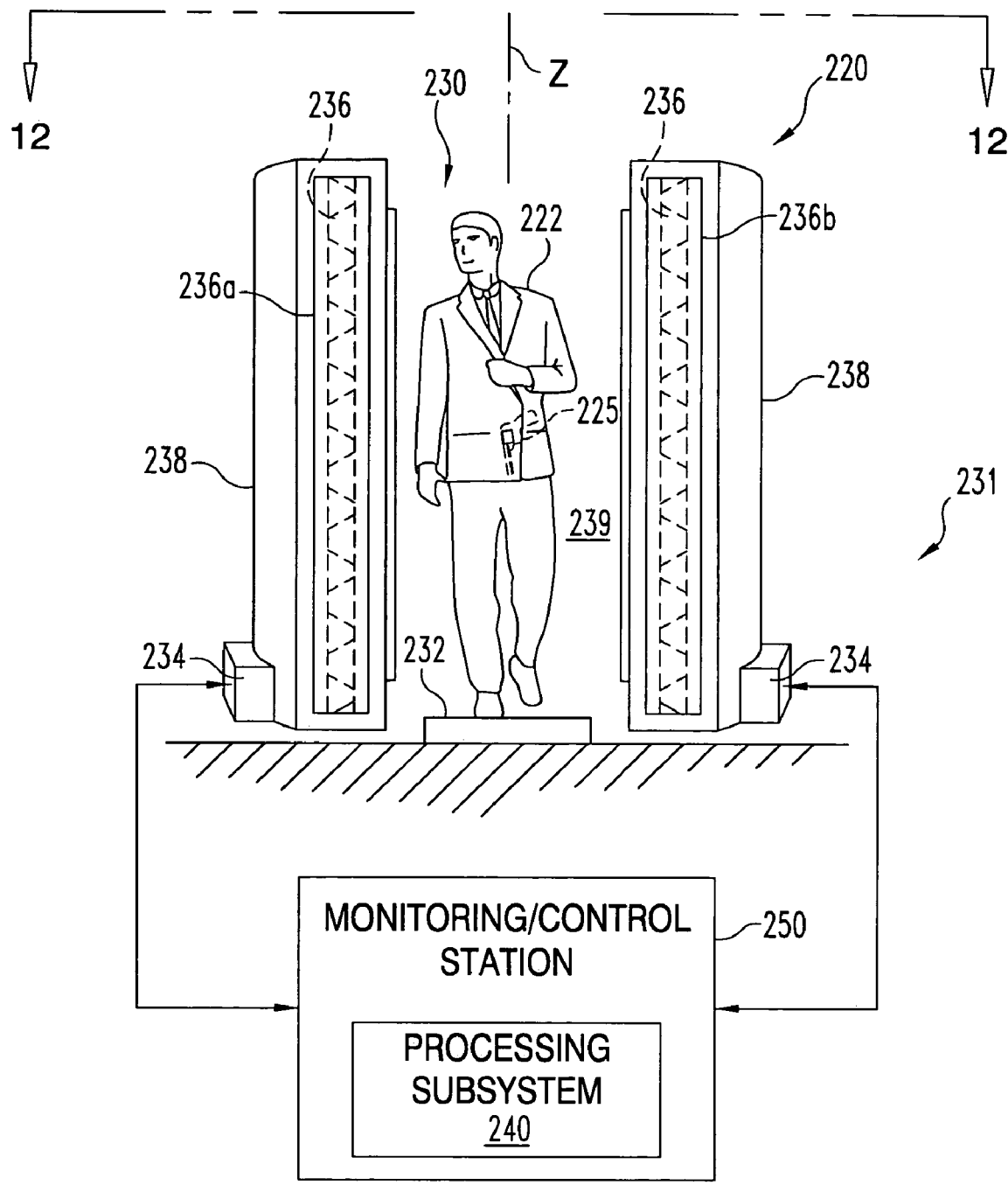
FIG. 11 is a partial, diagrammatic side view of a further system.
Figure 12:
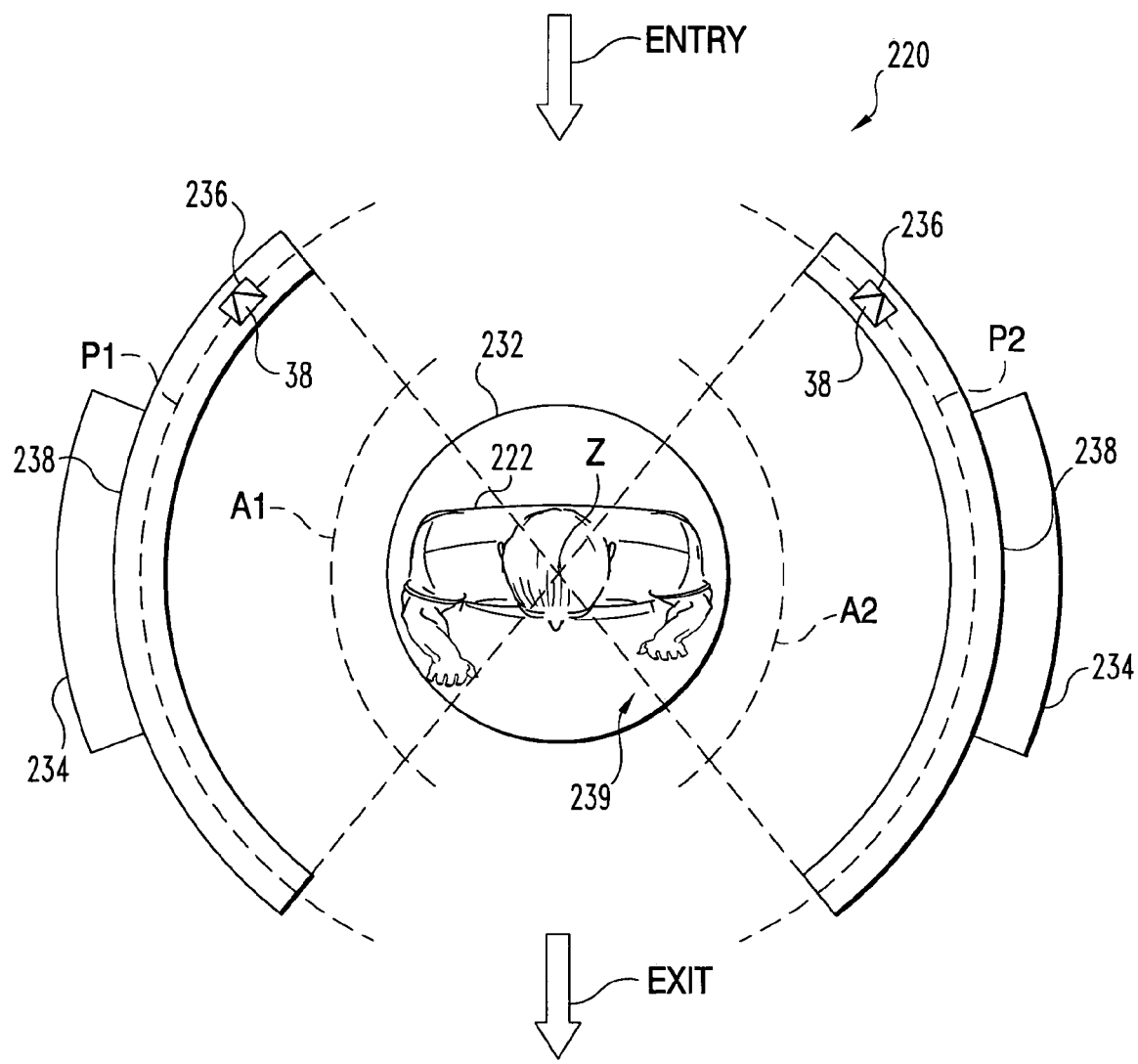
FIG. 12 is a partial, diagrammatic top view of the FIG. 11 system along the view line 12-12 shown in FIG. 11.

FIGS. 11 and 12 illustrate system 220 of a further embodiment of the present invention that can be used to perform procedure 120, routine 170a, routine 170b, and/or one or more operations described in connection with arrangement 200. System 220 illuminates person 222 with selected electromagnetic radiation in the matter described in connection with system 20. For system 220, person 222 is wearing clothing articles that conceal object 225 shown in phantom. As in the previously described embodiment of system 20, system 220 can be used to interrogate inanimate objects as well. System 220 includes dual clamshell panels 238 defining scanning portal 230 at security checkpoint 231.

System 220 also includes monitoring/control station 250 that is typically attended by one or more operators and coupled to panels 238 of portal 230. Station 250 includes processing subsystem 240. Subsystem 240 can be configured the same as subsystem 40, accounting for differences in scanning techniques of portal 230, as is more fully described hereinafter. Station 250 also includes one or more operator input and output devices (not shown) as described in connection with system 20 that are coupled to subsystem 240. Portal 230 includes stationary platform 232 arranged to support person 222. Platform 232 can be made of a material that is generally transparent to interrogation radiation. Portal 230 also includes an array 236 and a motor/drive mechanism 234 for each of panels 238. Array 236 is comprised at a column of elements 38 as described in connection with system 20. Mechanism 234 and arrays 236 are mechanically coupled to each other and are operatively coupled to subsystem 240. Under the control of subsystem 240, motor/drive mechanism 234 is configured to controllably move each of arrays 236 along a corresponding travel path P1 or P2 as best illustrated in FIG. 12. Notably, paths P1 and P2 are of a nonstraight, curvilinear type turning about axis Z. Axis Z is represented by crosshairs in FIG. 12 and corresponds to the vertical direction as best illustrated in FIG. 11. Correspondingly, arrays 236 each follow a path that turns about an interrogation region 239 including platform 232 and person 222, when driven by the respective mechanism 234. Alternatively or additionally, either or both of paths P1 and P2 could comprised of at least one straight path segment coupled to at least one other path segment in a curvilinear or angular manner. In still another arrangement, one or more of paths P1 and P2 are comprised of a number of straight path segments coupled together from one to the next at oblique angles to collectively turn about a portion of the interrogation region. In one particular form of this arrangement, the path segments are oriented to approximate an arc or other curvilinear shape. Further, while paths P1 and P2 are generally the same length and symmetric about axis Z, in other embodiments paths P1 and P2 may not be the same length and/or may not be symmetric. In one alternative variation, more than two panels, arrays, and corresponding paths are utilized.

Mechanism 234 can include an electric motor or other controlled prime mover to drive a conveying arrangement for the respective array 236. Such an arrangement could include a belt drive, a chain drive, a roller drive, or such other mechanized linkage as would occur to those skilled in the art to selectively move array 236. In other embodiments, a single prime mover may be utilized to which multiple arrays 236 in different panels are mechanically linked together to move in tandem. In further embodiments, another scanning arrangement could be utilized to transmit and/or receive the desired range of electromagnetic energy.

In system 220, subsystem 240 is configured the same of subsystem 40 of system 20, and is likewise arranged to perform procedure 120, routine 170a, routine 170b, and/or one or more of the operations described in connection with arrangement 200; and can include one or more transceivers and/or switching trees as appropriate. However, the operation of subsystem 240 does not provide for interrogation completely about the circumference of person 220. Instead, interrogation is performed over a partial circumference of less the 360°. The interrogation performed corresponds to angles A1 and A2 subtended by paths P1 and P2 as followed by arrays 236. In one preferred embodiment, angles A1 and A2 are each at least 90°. In a more preferred embodiment, angles A1 and A2 are each 120° or less. In a further preferred embodiment, angles A1 and A2 collectively provide a circumference scan coverage of at least 240° about region 239. System 220 can include one or more encoders (not shown) operably coupled to system 240 and/or other devices/techniques to track position of arrays 236 relative platform 232. System 220 can further include a communication subsystem (not shown) the same as subsystem 60 to remotely communicate with subsystem 240.

In one particular arrangement, panels 238 are shaped and configured to house a respective one of arrays 236 that each are about seven feet in height, include 224 elements 38, and operate in the 10 to 20 GHz frequency range. More specifically, arrays 236 each include two subarrays of 112 elements 38 each. For each array 236, the corresponding subarray pair is arranged back-to-back. This arrangement utilizes two ultrawide transceivers, and two corresponding switching trees, one for each of arrays 236, to selectively transmit with one element 38 and receive with another element 38 in a desired sequence. A high-speed computer within subsystem 240 controls mechanisms 234, arrays 236, the tranceivers, and the switching trees to obtain topographical data for processing. Panels 238 are opposite one another to provide an angular scanning range of about 240° for this arrangement. In one mode of operating this system, a person 222 under surveillance enters along the "ENTRY" arrow into region 239 between panels 238. Person 222 then turns and faces one of panels 238 for one to two seconds while arrays 236 move along paths P1 and P2 to perform the, scan. Person 222 then turns and exits along the "EXIT" arrow after scanning. It is has been found that the 240° coverage provided by this approach is suitable to detect most objects that pose a threat to security. Panels 238 are each made to be at least partially transparent to facilitate viewing therethrough by an operator during the interrogation of person 222 in region 239.

Figure 13:
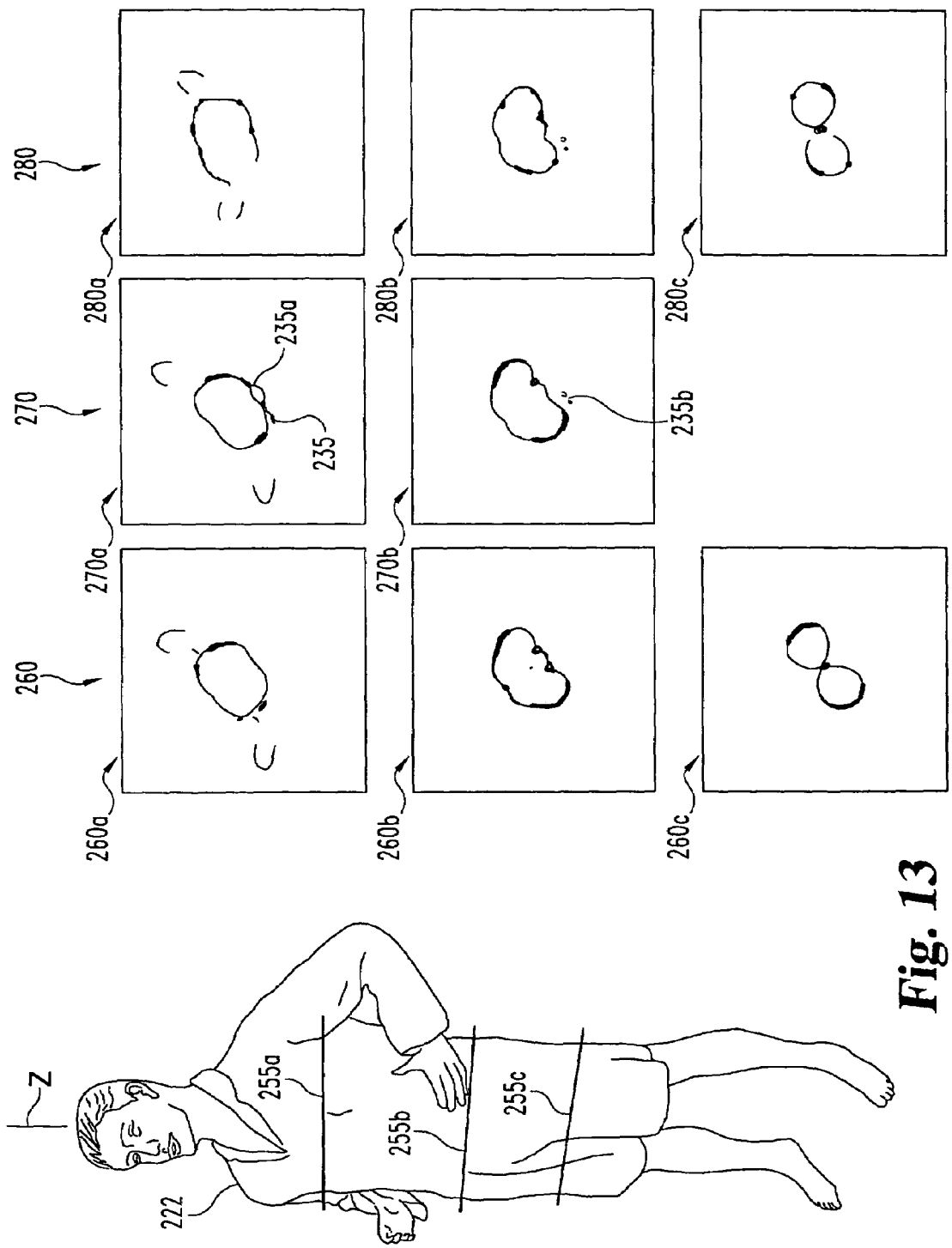
FIG. 13 is a comparative diagram illustrating cross-sectional images generated in accordance with various techniques of the present invention.

Referring to FIG. 13, cross-sectional images of mannequin 222a are shown as produced by laboratory simulation experiments performed in accordance with the present invention. Such cross-sectional images facilitate the detection of suspicious objects while reducing the likelihood of providing images to which a privacy objection might be made. Mannequin 222a is imaged in a number of views in the columns 260, 270, and 280 that were taken with respect to different section lines 255a, 255b, and 255c of mannequin 222a. Cross-sectional images 260a, 270a, and 280a correspond to sections taken along section line 255a and transverse to axis Z. Likewise, cross-sectional images 260b, 270b, and 280b correspond to sections taken along section line 255b and transverse to axis Z. Further, cross-sectional images 260c and 280c correspond to sections taken along section line 255c and transverse to axis Z. The cross-sectional images 260a, 260b, and 260c shown in column 260 each correspond to a cross-sectional view along axis Z in which there is no object being carried and in which a full, 360° circumference is imaged. Images 270a and 270b of column 270 also provide full, 360° circumference cross-sections and further depict various threats concealed by clothing. Specifically, in cross-sectional image 270a, a small handgun 235 and dielectric slab 235a are detected. In cross-sectional image 270b, hand grenade 235b is detected. Images 280a, 280b, and 280c of column 280 each depict a 240-degree partial circumference view corresponding to one arrangement of system 220. In this system, the incomplete coverage (partial circumference) still reveals hand grenade 235d. It has been found that the arrangement of system 220 with less than 360° coverage provides a faster scanning and processing time that may be desirable in certain applications.

For this particular experimental arrangement of system 220, panels 238 are operated in an FM/CW mode with a 10-20 GHz sweep in less than 20 microseconds to provide an imaging resolution of about 1 centimeter and a range resolution of about 1.5 centimeters. During operation in this manner, arrays 236 are each provided in the form of two vertically-oriented subarrays arranged back-to-back. One subarray is dedicated to transmission and the other to reception. In one form, each subarray is fabricated with 112 elements of the slot-line antenna type. For each subarray, the elements are spaced apart from one another by a uniform distance. During operation, each subarray is electronically scanned from element-to-element as the scanner moves rapidly over the generally horizontal travel path P1 or P2. As the array moves, a number of scans are performed with only one element transmitting at a time and only one receiving reflective electromagnetic radiation due to such transmission. Each transmitting element and each receiving element is activated in accordance with a desired sequence during the scan. Nonetheless, in still other embodiments, a different number, size, or type of linear array arrangement can be utilized as would occur to those skilled in the art. In still other examples, different types of rotating and/or linear scanning arrays can be utilized separately or in combination. Further, as an alternative or addition to cross-sectional images, other types of images and/or automatic concealed object detection techniques can be utilized as described in connection with the embodiments of FIGS. 1-10 to address privacy concerns.

Figure 14:
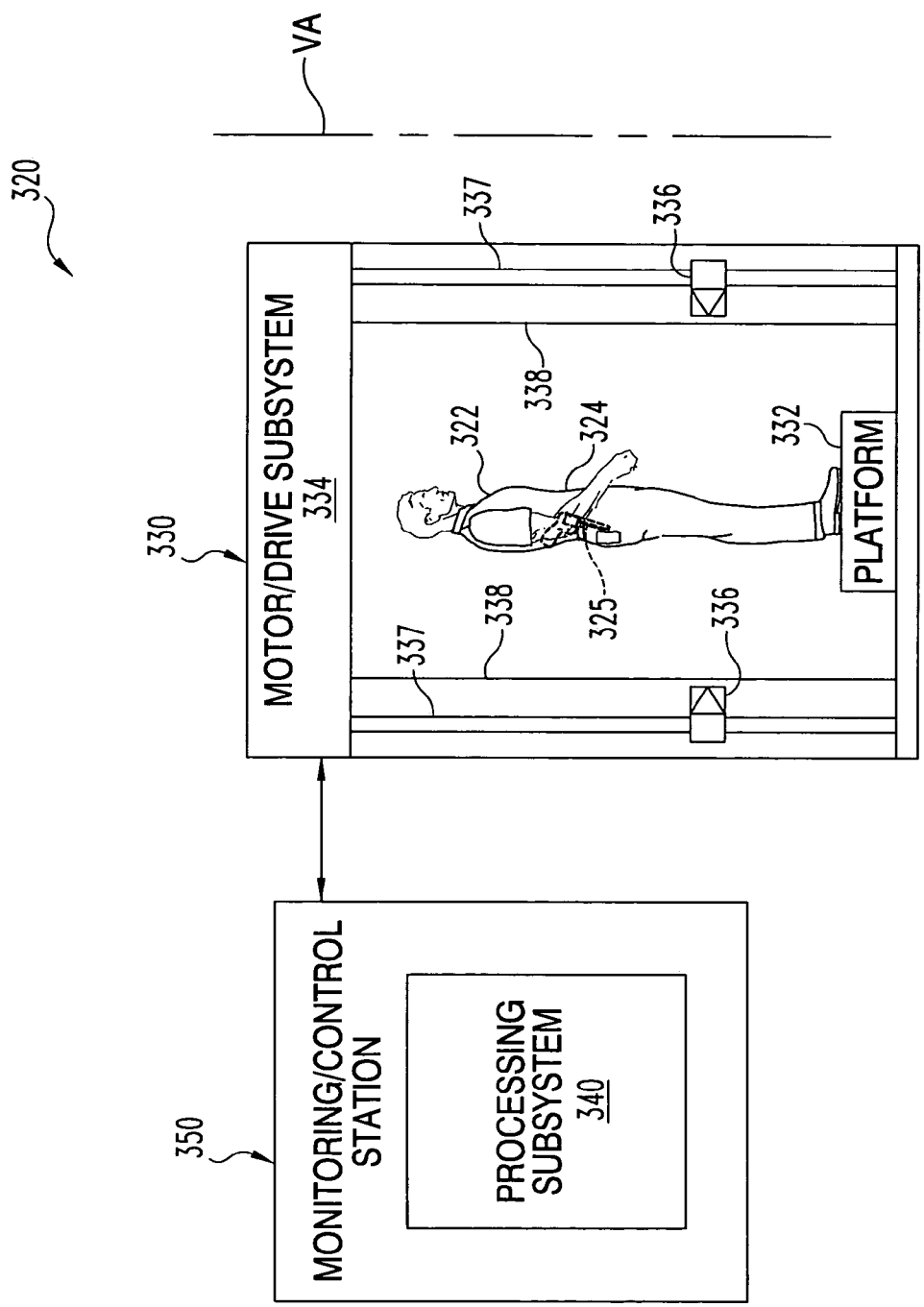
FIG. 14 is a partial, diagrammatic view of another system.
Figure 15:
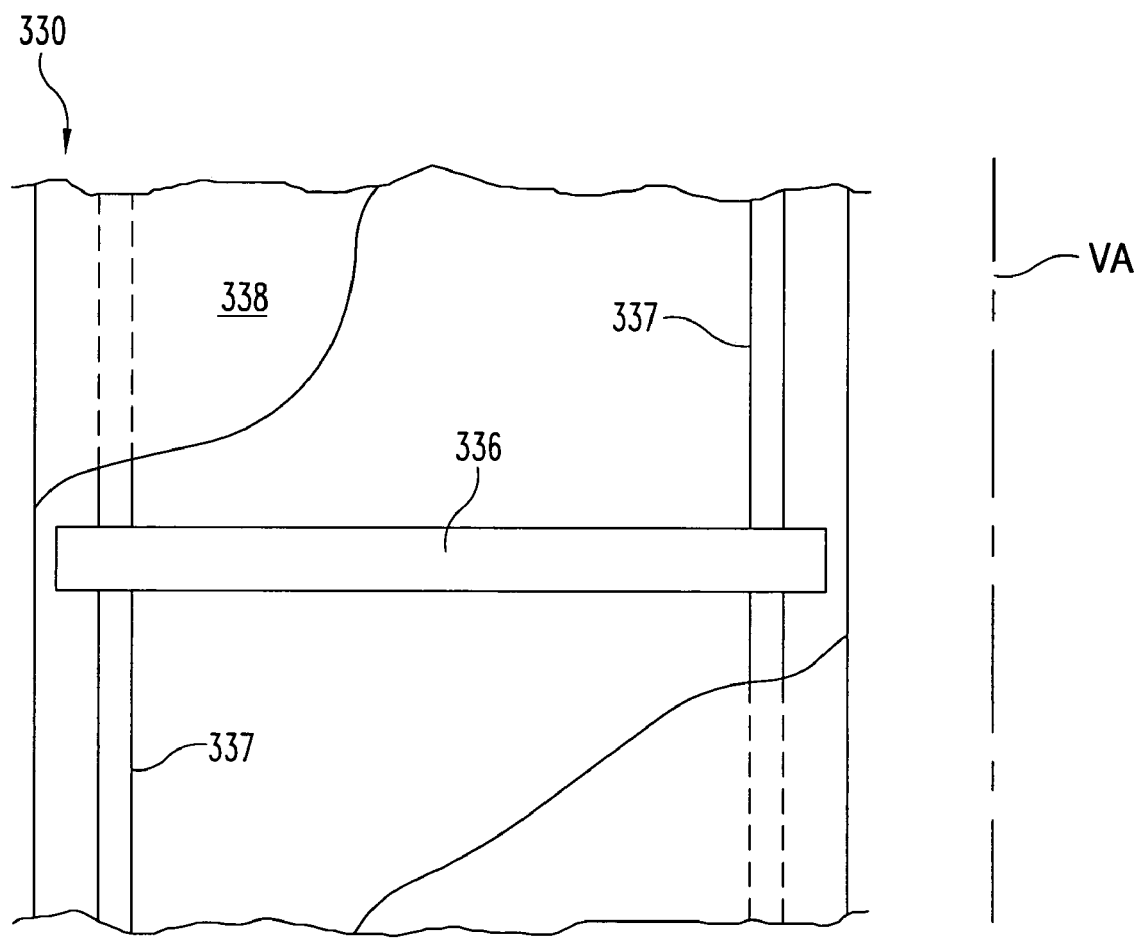
FIG. 15 is a partial, cut-away view of the portal shown in FIG. 14.

FIGS. 14 and 15 illustrate system 320 of another embodiment of the present invention that can be used to perform procedure 120, routine 170a, routine 170b and/or one or more operations of arrangement 200 as described in connection with FIG. 10. System 320 illuminates person 322 which selected electromagnetic radiation in the manner described in connection with system 20. For system 320, person 322 is wearing clothing articles that conceal object 325 shown in phantom. As in the previously described embodiments, system 320 can be used to interrogate inanimate objects as well. System 320 includes dual planar panel scanning portal 330 and processing subsystem 340 included in monitoring/control station 350. Portal 330 is coupled to processing subsystem 340 and can be configured the same as subsystem 40, accounting for differences in the scanning technique of portal 330 as is more fully described hereinafter. Station 350 includes one or more operator input and output devices as described in connection with system 20 that are coupled to subsystem 340. Station 350 can be arranged to provide a security checkpoint operator interface adjacent portal 330.

Portal 330 includes stationary platform 332 arranged to support person 322 and overhead motor/drive subsystem 334. Under the control of subsystem 340, subsystem 334 is configured to controllably slide each of two arrays 336 along corresponding guide rods 337 up-and-down with respect to vertical axis VA. Correspondingly, arrays 336 each follow a generally straight, linear path on opposite sides of person 322 and are each included within a corresponding opposing panel 338. FIG. 15 shows one of panels 338 in greater detail utilizing a partial cut-away view. In system 320, subsystem 340 is configured the same as subsystem 40 of system 20 to perform generally the same operations previously described and can include a transceiver and/or switching tree as appropriate. However, in contrast to system 20, the operation of subsystem 340 accounts for the movement of array 336 relative to person 322 in a linear, translational manner instead of a rotational manner as described in connection with system 20. System 320 can include one or more encoders (not shown) operably coupled to system 340 and/or other devices/techniques to track position of arrays 336 relative to platform 332. System 320 can further include a communication subsystem (not shown) the same as subsystem 60 to remotely communicate with subsystem 340.

In one particular arrangement, panels 338 are spaced apart by about 1.22 meters and a frequency sweep in the Ku-band from about 12.5-18 GHz is performed to provide a lateral resolution of about 1 centimeter and a depth resolution of about 2.7 centimeters. For this arrangement, arrays 336 each include two subarrays of about 56 elements each that are arranged back-to-back. One subarray is dedicated to transmission and the other subarray is dedicated to reception within each array 336. In one form, each subarray is fabricated with slot-line antennas spaced apart from one another by about 2 centimeters. During operation, each subarray is electronically scanned from element-to-element as the scanner moves rapidly over the vertical length of person 322. As the array moves, a number of scans are performed with array 336. During each scan, only one element of the transmitting subarray is illuminating the person and only one element of the receiving subarray is collecting reflected electromagnetic radiation at any given time. Accordingly, each transmitting element and each receiving element is activated in accordance with a desired sequence during the scan. In a FM/CW heterodyne transceiver configuration of this arrangement, the 5.5 GHz frequency sweep is performed in about 12.75 microseconds. In one form, system 320 may not include the generation of a topographical representation and/or frames at operation 162, such that frame-to-frame consistency checking described in connection with routine 170a and 170b is not performed. In still other embodiments, a different number, size, or type of linear array arrangement can be utilized as would occur to those skilled in the art. In still other examples, different types of rotating and/or linear scanning arrays can be utilized separately or in combination. Furthermore, system 320 can be used to generate one or more cross-sectional views of person 322 and/or utilize one or more other approaches described in connection with the embodiments of FIGS. 1-10 to address privacy concerns.

Figure 16:
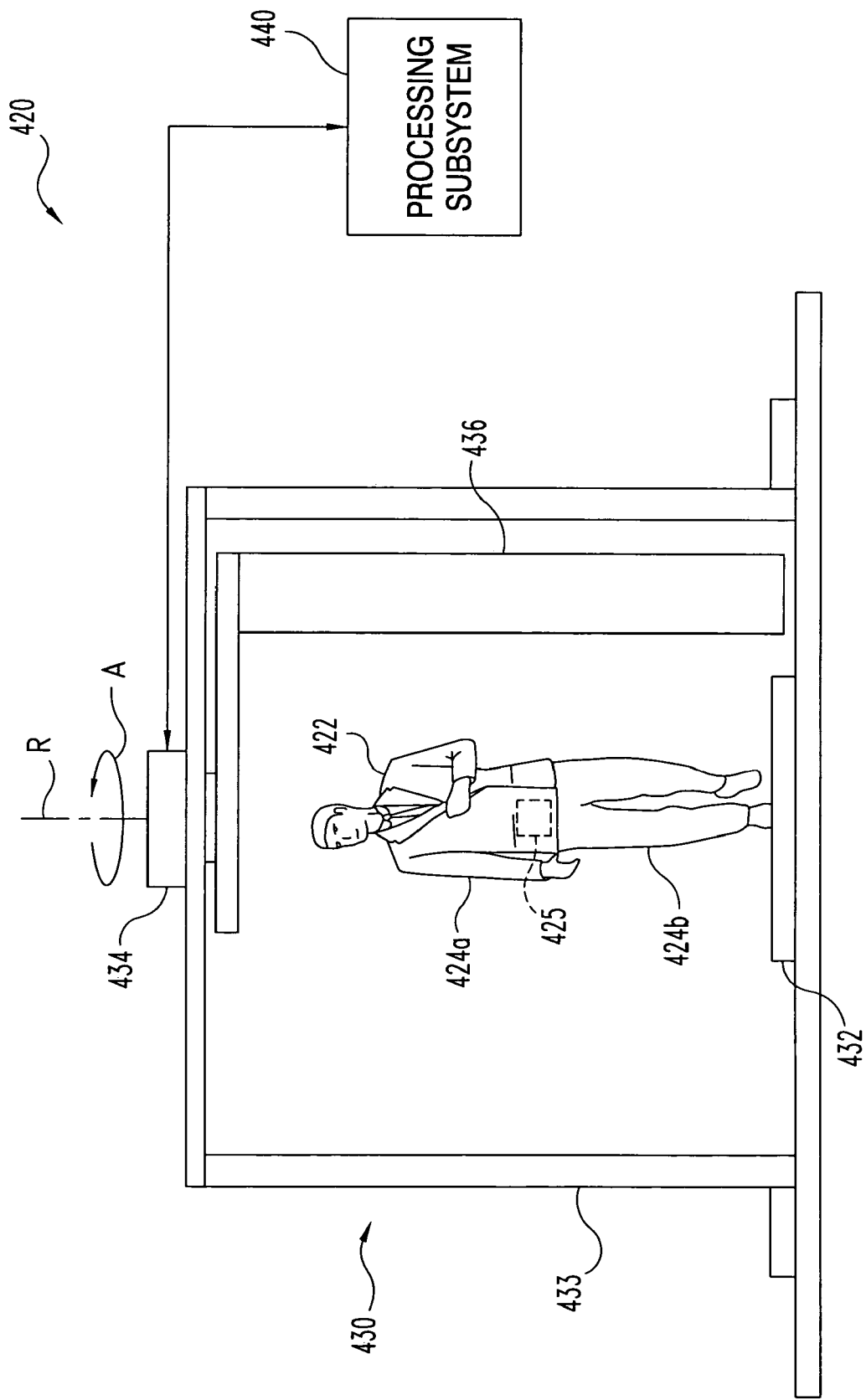
FIG. 16 is a partial, diagrammatic view of still another system.

FIG. 16 illustrates interrogation system 420 of another embodiment of the present invention. System 420 illuminates person 422 with selected electromagnetic radiation in the manner described in connection with system 20. For system 420, person 422 is wearing clothing articles 424a and 424b that hide object 425. As in previously described embodiments, system 420 can be used to interrogate inanimate objects as well.

System 420 includes scanning booth 430 coupled to control and processing subsystem 440. Scanning booth 430 includes stationary platform 432 arranged to support person 422 and frame 433 to support motor 434 coupled to array 436. In contrast to the platform rotation of portal 30 and translational movement associated with portal 330, scanning booth 430 selectively rotates array 436 about rotational axis R and platform 432 during interrogation. For this arrangement, array 436 follows a generally circular pathway to provide a corresponding imaginary cylinder about platform 432. In one form suitable for scanning a person in the standing position, the radius of this cylinder is about 1 meter. Array 436 is otherwise configured the same as array 36.

In system 420, subsystem 440 is configured the same as subsystem 40 of system 20 and is likewise arranged to perform procedure 120, routine 170a, routine 170b, and/or one or more operations of arrangement 200 to detect objects that may pose a threat to security. However, the operation of subsystem 440 accounts for the movement of array 436 relative to platform 432 instead of the movement of platform 32 relative to array 36 as for system 20. System 420 can include one or more encoders (not shown) operatively coupled to subsystem 440 and/or other devices/techniques to track the position of array 436 relative to platform 432. System 420 can further include a communication subsystem (not shown) the same as subsystem 60 to remotely communicate with subsystem 440. System 420 can be used to generate one or more cross-sectional views of person 422 and/or utilize one or more other approaches described in connection with the embodiments of FIGS. 1-10 to address privacy concerns.

Figure 17:
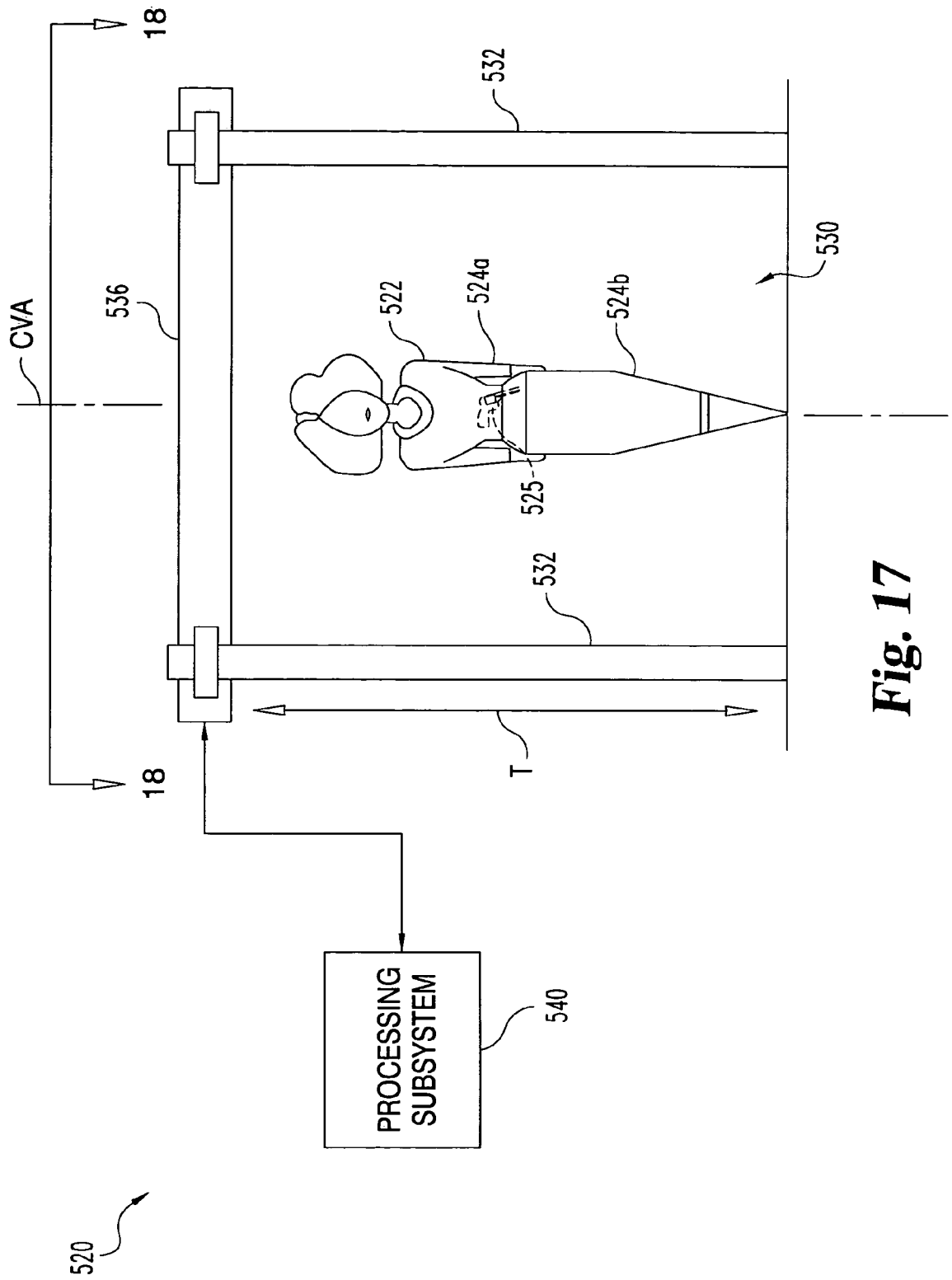
FIG. 17 is a partial, diagrammatic view of yet another system.

FIG. 17 illustrates electromagnetic radiation interrogation system 520 of yet another embodiment of the present invention. System 520 illuminates person 522 with selected electromagnetic radiation of the type previously described. For system 520, person 522 is wearing garments/clothing designated by reference numerals 524a and 524b that conceal object 525. As in previously described embodiments, system 520 can be used to interrogate animate or inanimate objects.

System 520 includes scanning booth 530 coupled to control and processing subsystem 540. Scanning booth 530 includes frame 533 arranged to receive person 522 and support array 536. In contrast to the linearly oriented arrays 36, 336, and 436 of previously described systems 20 and 420, array 536 is arranged as a ring or hoop generally centered with respect to centerline vertical axis CVA. A number of electromagnetic radiation transmitting/receiving elements are arranged in a generally circular pathway along the ring. These elements operate to interrogate person 522 with electromagnetic radiation including one or more wavelengths in the millimeter, microwave, and/or adjacent wavelength bands. Array 536 is arranged for translational movement along axis CVA to scan person 522 as represented by travel arrow T. One or more motors or other prime mover(s) (not shown) are utilized to selectively move array 536 along axis CVA.

Figure 18:
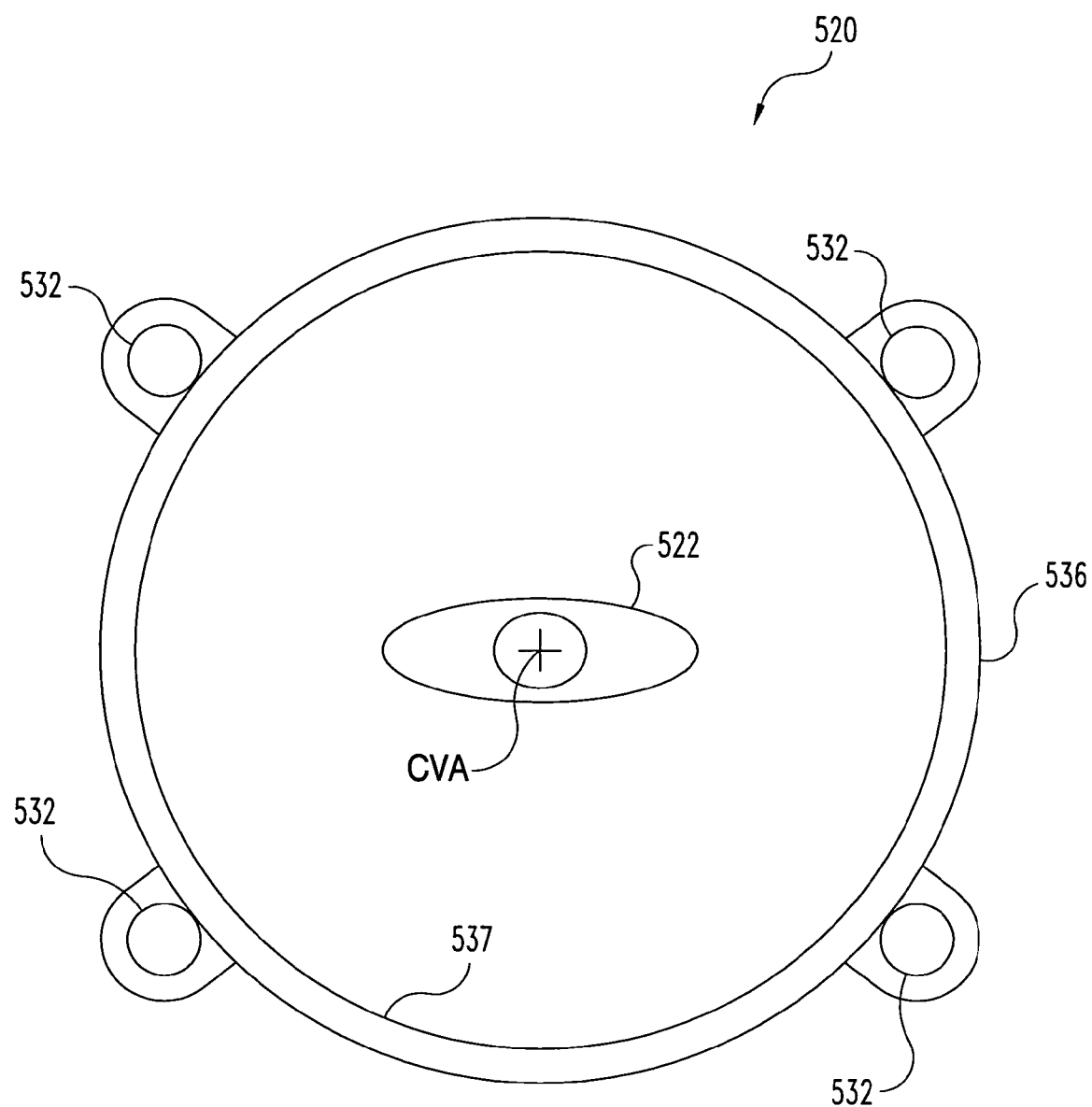
FIG. 18 is a partial, top view of the system of FIG. 17 along the view line 18-18 shown in FIG. 17.

Referring further to the partial top view of FIG. 18, array 536 is sized with opening 537 to receive person 522 therethrough as array 536 moves up and down along axis CVA. In FIG. 18, axis CVA is generally perpendicular to the view plane and is represented by crosshairs. With the vertical motion of array 536, an imaginary cylinder is defined about person 522 in accordance with the circular path defined by the array ring; however, neither person 522 nor array 536 is rotated relative to the other, instead translational movement of array 536 is used to scan person 522 vertically.

Subsystem 540 is configured the same as subsystem 40, and is operable to perform procedure 120, routine 170a, routine 170b, and/or one or more operations or arrangement 200, except that processing of subsystem 540 is adapted to account for the vertical translational movement of array 436 with its circumferential arrangement. System 520 can further include a communication subsystem (not shown) the same as subsystem 60 to remotely communicate with subsystem 540. Like previously described embodiments, system 520 is used to detect concealed objects as explained in connect with procedure 120.

Compared to array 36, a larger number of transmitting/receiving elements is typically needed for array 536 to have a comparable resolution to previously described embodiments. In one comparative nonlimiting example, between 500 and 2000 transmitting/receiving elements would be desired for array 536 versus 200 to 600 for array 36 for comparable resolution, depending on the frequency band selected. However, under appropriate conditions, scanning booth 530 can perform a scan substantially faster than portal 30. In one nonlimiting example, the scan time for portal 30 is in a range of about 10 to 20 seconds versus about 2 to 5 seconds for scanning booth 530. System 520 can be used to generate one or more cross-sectional views of person 522 and/or utilize one or more other approaches described in connection with FIGS. 1-10 to address privacy concerns.

In a further embodiment of the present invention, the body undergoing interrogation and the array both move. In one such example, array elements are arranged in an arc segment that can move vertically while the body rotates. In other examples, both the array and body rotate and/or translationally move. The processing of interrogation data can be adjusted for these different motion schemes using techniques known to those skilled in the art.

As described in connection with system 220, the interrogation and corresponding image information may not correspond to the full circumference of the body undergoing interrogation. Instead, the segment of interest can be less than 360 degrees. For such embodiments, the image information can be interpolated by combining data corresponding to two or more different view angles. Alternatively or additionally, less than the full height, width, and/or length of the subject may be scanned in other embodiments. For such alternatives, the array size and/or scanning pattern can be correspondingly adjusted.

In still other embodiments of the present invention, the image data gathered with system 20, 220, 320, 420, and/or 520 corresponds to a number of cylindrical images without combining some or all of the images together to provide a topographical representation. Instead, the cylindrical images are used without being combined or only partially being combined. In yet other embodiments, imaging may be completely or partially noncylindrical in nature with or without a degree of combining to provide a topographical representation. In one particular case, the planar panels of system 320 may provide planar, instead of cylindrical image information without multiple frames.

In one further embodiment, the image information is obtained in accordance with procedure 120, routine 170*a*, routine 170*b*, arrangement 200, system 20, system 220, system 320, system 420, and/or system 520 is additionally utilized to identify an individual. One form of this embodiment includes a technique to control access to a restricted area, comprising: scanning an individual attempting to gain access to the restricted area; determining whether the individual is concealing any objects from the scan; comparing one or more aspects of the corresponding image information regarding features of the individual to data stored for those permitted access to the restricted area; and allowing access to the restricted area by the individual if there is a favorable comparison and no suspicious concealed objects are indicated. The determination of a match can be used to activate a gate or other access control device.

In another embodiment, image information gathered in accordance with procedure 120, routine 170*a*, routine 170*b*, arrangement 200, system 20, system 220, system 320, system 420, and/or system 520 is additionally or alternatively used to identify individuals for which access should not be permitted, such as suspected criminals, known terrorists, and the like. In one more variation of such embodiments, one or more other biometrics (such as a fingerprint, palm print, retina image, vocal pattern, etc.) of the individual are compared in addition to the topographical representation data as part of the determination of whether to allow access. The features used for identification can be changed for each access to reduce the likelihood that the access control measures will be circumvented. Alternatively or additionally, object detection in accordance with the present invention can be used to determine if an individual is taking an object from an area without permission to do so. Any of these embodiments can be provided as a method, apparatus, system, and/or device.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A method, comprising:
   detecting electromagnetic radiation returned from a concealed surface associated with a person, the electromagnetic radiation including one or more frequencies in a range of about 200 MHz to about 1 THz;
   establishing data corresponding to intensity of the returned electromagnetic radiation along the surface and depth along the surface; and
   adaptively processing the data to determine if a man-made object suspected to be one or more of contraband or a potential security threat is being carried by the person as a function of the intensity along the surface and the depth along the surface.

2. The method of claim 1, wherein the said adaptively processing operates with a map of surface depth difference to determine if the man-made object is being carried by the person as the function of the depth along the surface.

3. The method of claim 1, which includes applying a median filter and one or more morphological filters.

4. The method of claim 1, which includes comparing a first image frame data set to a second image frame data set.

5. The method of claim 1, wherein the object is at least one weapon.

6. The method of claim 1, which includes:
   irradiating the person with an electromagnetic radiation output from a transducer array; and
   displaying relative location of the man-made object on a image representative of the person.

7. The method of claim 1, wherein said adaptively processing is performed for each of a number of image portions, the image portions each corresponding to a group of image pixels.

8. The method of claim 7, wherein said adaptively processing further includes:
   utilizing a neural network to process each of the image portions;
   for each of a first set of inputs of the neural network, receiving an image pixel intensity input in correspondence to the image pixels of the group for a respective one of the image portions;
   for each of a second set of inputs of the neural network, receiving a depth difference input from the respective one of the image pixels of the designated group for the one of the image portions; and
   comparing an output from the neural network to a threshold to determine if the object is suspected.

9. A method, comprising:
   irradiating an interrogation region including a person carrying a concealed object;
   detecting electromagnetic radiation returned from the interrogation region in response to said irradiating, the electromagnetic radiation including one or more frequencies in a range of about 200 MHz to about 1 THz;
   establishing data representative of a map of intensity of the electromagnetic radiation returned from the interrogation region and a map of depth along the interrogation region; and
   inputting the data into a neural network to determine if the concealed object is at least one of contraband or a weapon based on the map of intensity and the map of depth.

10. The method of claim 9, which includes:
    applying one or more morphological filters to image output data from the neural network; and
    comparing a first neural network image output for a first image frame to a second neural network image output for a second image frame.

11. The method of claim 9, which includes:
    evaluating each of a number of different image data portions with the neural network to determine if the concealed object is present, the image data portions each corresponding to a different group of image pixels, the data representative of the map of intensity corresponding to a two-dimensional map of image pixel intensity;

calculating a two-dimensional map of pixel range as a function of temporal information determined in relation to said irradiating and said detecting; and determining the data representative of the map of depth in accordance with depth difference based on the two-dimensional map of pixel range.

12. The method of claim 11, which includes displaying relative location of the concealed object on a image representative of the person.

13. The method of claim 9, which includes displaying relative location of the concealed object on a image representative of the person.

14. The method of claim 9, wherein said interrogating includes scanning the person in a portal at a security checkpoint with incident electromagnetic radiation and said establishing includes generating image data corresponding to a number of cylindrical images.

15. The method of claim 9, wherein said establishing includes generating information corresponding to one or more cylindrical images of the person.

16. The method of claim 9, which includes adaptively processing a spatial frequency representation corresponding to at least a portion of an image of the person.

17. A system, comprising:

an array operable to interrogate a person with electromagnetic radiation at one or more frequencies in a range of about 200 MHz to about 1 THz; and a processing subsystem coupled to the array, the processing subsystem being operable to provide a neural network including a first set of inputs and a second set of inputs, the first set of inputs being arranged to receive data corresponding to a map of returned electromagnetic radiation intensity along a surface beneath clothing of the person, the second set of inputs being arranged to receive other data corresponding to a map of depth along the surface, the neural network being effective to evaluate if one or more objects suspected of being at least one of contraband or a potential security threat as a function of the map of intensity and the map of depth are concealed by the person and provide one or more corresponding outputs.

18. The system of claim 17, wherein the neural network is of a multilayer perceptron type.

19. The system of claim 17, wherein the map of depth is representative of depth difference and the processing subsystem include means for determining the map of depth from a map of range information.

20. The system of claim 17, further comprising a display device responsive to the one or more outputs to provide at least one image if presence of the one or more objects is indicated.

21. The system of claim 17, wherein the processing subsystem includes means for filtering image information.

22. The system of claim 17, wherein the array is provided in a first panel and further comprising another array in a second panel coupled to the processing subsystem, and the first panel and the second panel are arranged to provide a security checkpoint portal.

23. The system of claim 17, further comprising a platform proximate to said array to support the person and a motor to move at least one of the array and the platform relative to another of the array and the platform to perform a security scan of the person at a security checkpoint.

24. The system of claim 17, wherein the processing subsystem is further operable to generate image data corresponding to a number of cylindrical images of the person.

25. An apparatus, comprising:

a device carrying logic executable by one or more processors to analyze data corresponding to an image of a person obtained from electromagnetic radiation including one or more frequencies in a range of about 200 MHz to about 1 THz, the data being representative of a map of electromagnetic radiation intensity and a map of depth determined relative to the person, the logic being further operable to execute an adaptive process with the data to evaluate if one or more objects suspected of being at least one of contraband or a potential security threat are being concealed by the person as a function of the map of electromagnetic radiation intensity and the map of depth and provide an output indicating the detection of the one or more objects if indicated by the adaptive process.

26. The apparatus of claim 25, wherein the device is in the form of a processor-readable memory and the logic is in the form of a number of instructions stored in the memory.

27. The apparatus of claim 25, wherein the device includes one or more parts of a computer network and the logic is encoded in one or more signals for transmission over the computer network.

28. The apparatus of claim 25, wherein the logic is further operable to determine the map of depth as a depth difference map.

29. The apparatus of claim 28, wherein the logic defines at least one neural network.

30. The apparatus of claim 29, wherein the logic defines means for filtering image pixel information.

31. A method, comprising:

establishing a first data set corresponding to intensity of returned electromagnetic radiation from an object along a surface of the object and a second data set corresponding to depth along the surface; and adaptively processing the first data set and the second data set to identify a man-made object suspected to be one or more of contraband or a potential security threat.

* * * * *